US008895696B1

(12) United States Patent
Sucheck et al.

(10) Patent No.: US 8,895,696 B1
(45) Date of Patent: Nov. 25, 2014

(54) METHODS FOR FORMING PEPTIDES AND PEPTIDE CONJUGATES AND PEPTIDES AND PEPTIDE CONJUGATES COMPOSITIONS FORMED THEREBY

(75) Inventors: Steven J. Sucheck, Maumee, OH (US); Rommel S. Talan, Louisville, KY (US); Partha Karmakar, Toledo, OH (US)

(73) Assignee: The University of Toledo, Toledo, OH (US)

( * ) Notice: Subject to any disclaimer, the term of this patent is extended or adjusted under 35 U.S.C. 154(b) by 104 days.

(21) Appl. No.: 13/596,954

(22) Filed: Aug. 28, 2012

Related U.S. Application Data

(60) Provisional application No. 61/529,435, filed on Aug. 31, 2011.

(51) Int. Cl.
*C07K 2/00* (2006.01)
*C07K 1/06* (2006.01)
*C07K 1/113* (2006.01)
*C07K 1/36* (2006.01)
*C07K 5/103* (2006.01)
*C07D 207/16* (2006.01)
*C07K 9/00* (2006.01)
*C07C 311/19* (2006.01)
*C07K 1/107* (2006.01)
*C07D 233/64* (2006.01)
*C07K 5/062* (2006.01)
*C07K 7/06* (2006.01)

(52) U.S. Cl.
CPC .............. *C07K 1/1075* (2013.01); *C07K 5/101* (2013.01); *C07D 207/16* (2013.01); *C07K 9/001* (2013.01); *C07C 311/19* (2013.01); *C07D 233/64* (2013.01); *C07K 5/0606* (2013.01); *C07K 7/06* (2013.01)
USPC ........... 530/322; 530/300; 530/333; 530/334; 530/336

(58) Field of Classification Search
CPC .......... C07K 1/00; C07K 1/003; C07K 1/006; C07K 1/02; C07K 1/04; C07K 1/06; C07K 1/061; C07K 1/063; C07K 1/64; C07K 1/107; C07K 1/1072; C07K 1/1075; C07K 2/00; C07K 9/001; C07K 5/101; C07K 5/0606; C07C 311/19; A61K 8/30; A61K 8/466; A61K 8/46; A61K 8/49; A61K 8/4906; A61K 8/4926; A61K 8/4946; A61K 8/4953; A61K 8/40
See application file for complete search history.

(56) References Cited

FOREIGN PATENT DOCUMENTS

| WO | WO 2008/066186 | * | 6/2008 | ............... C07K 1/02 |
| WO | WO 2008/066816 | * | 6/2008 | ............... C07K 1/02 |

OTHER PUBLICATIONS

De Luca et al., Tetrahedron Letters (2005) 46, 6637-6640.*
Talan, Dissertation "Chemical Ligation of Glycopeptides" (Aug. 2010) University of Toledo, 1-375.*
Fukuyama et al., Tetrahedron Letters (1997) 38(33), 5831-5834.*
Holguin, Dissertation, Masters of Science (1979) University of British Columbia: Vancouver, Canada.*

* cited by examiner

*Primary Examiner* — Karlheinz R Skowronek
*Assistant Examiner* — Catherine Mader
(74) *Attorney, Agent, or Firm* — MacMillan, Sobanski & Todd, LLC

(57) ABSTRACT

Methods for building peptide chains containing sulfonyl modified amines at the N-terminus, or, within amino acid side chains, of a growing peptide in a solid-phase peptide synthesis are described. Further, compositions having a sulfonyl modified amine attached to the N-terminus, or within an amino acid side chain, of a polypeptide containing three or more amino acid residues are described.

26 Claims, 30 Drawing Sheets

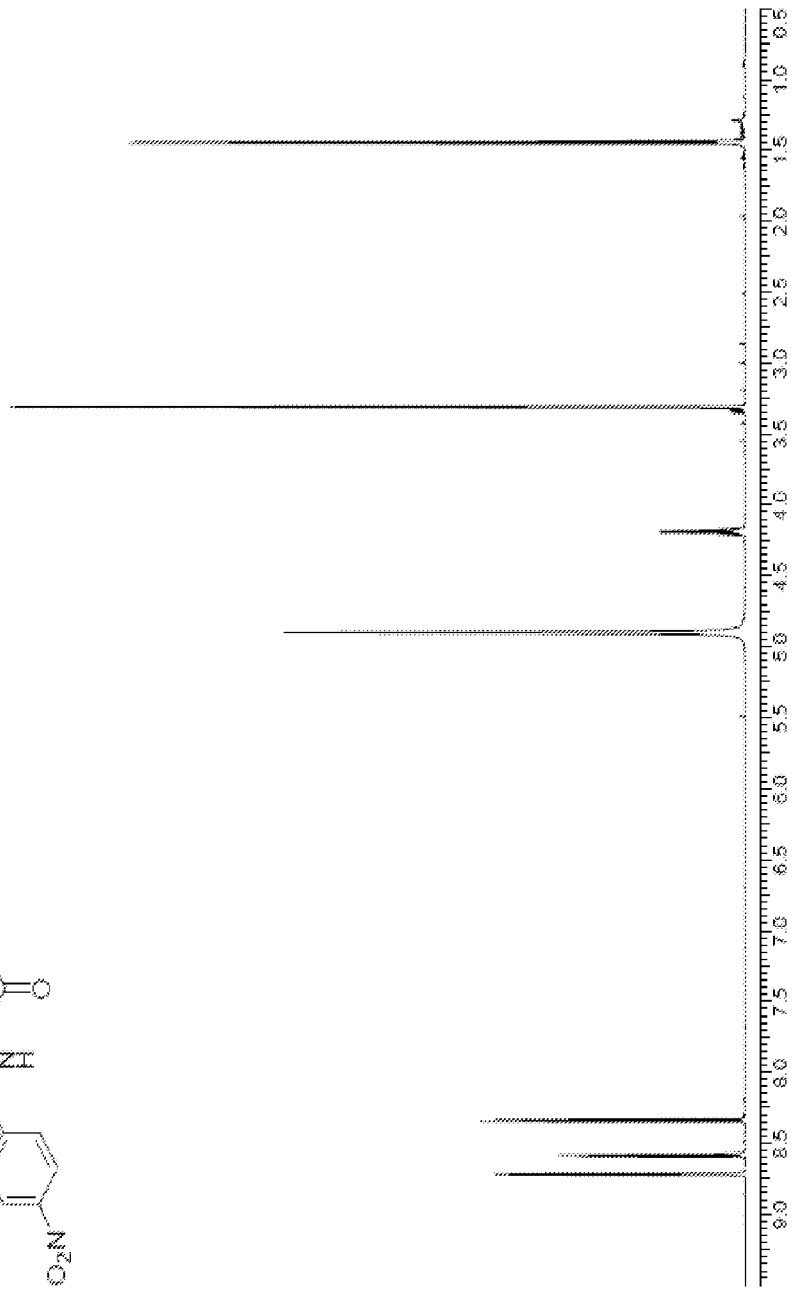
Figure 1. ¹H NMR of dNDS-Alanine (1).

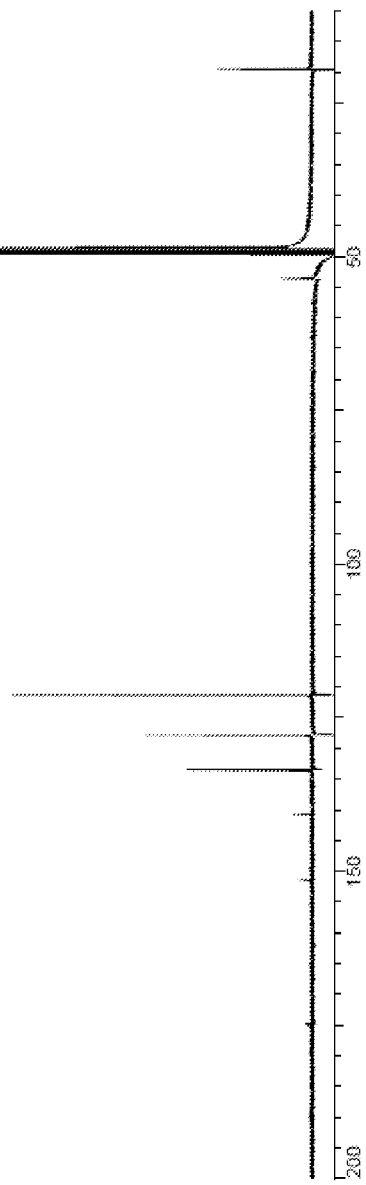
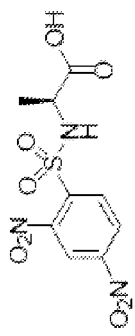
Figure 2. $^{13}$C NMR of dNBS-Alanine (1).

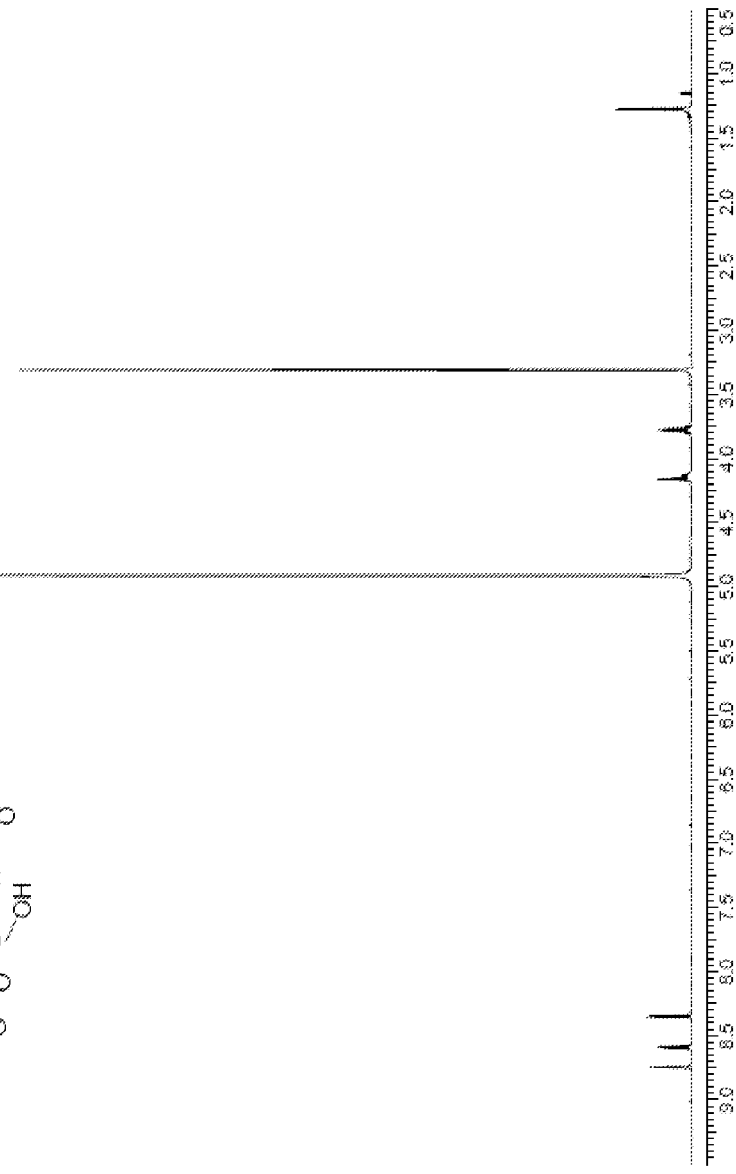
Figure 3. ¹H NMR of dNBS-Ser-Ala-OH (2).

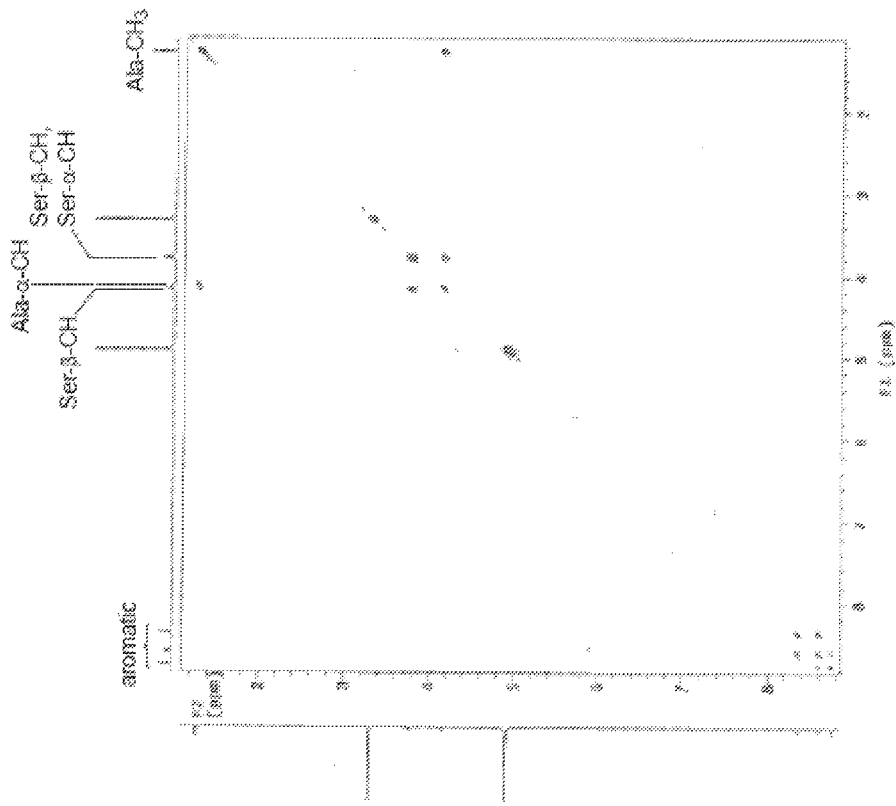
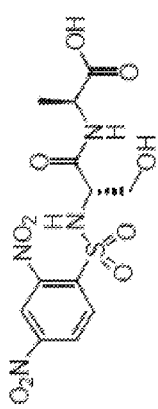
Figure 4. $^1$H-$^1$H gCOSY NMR of dNBS-Ser-Ala-OH (2)

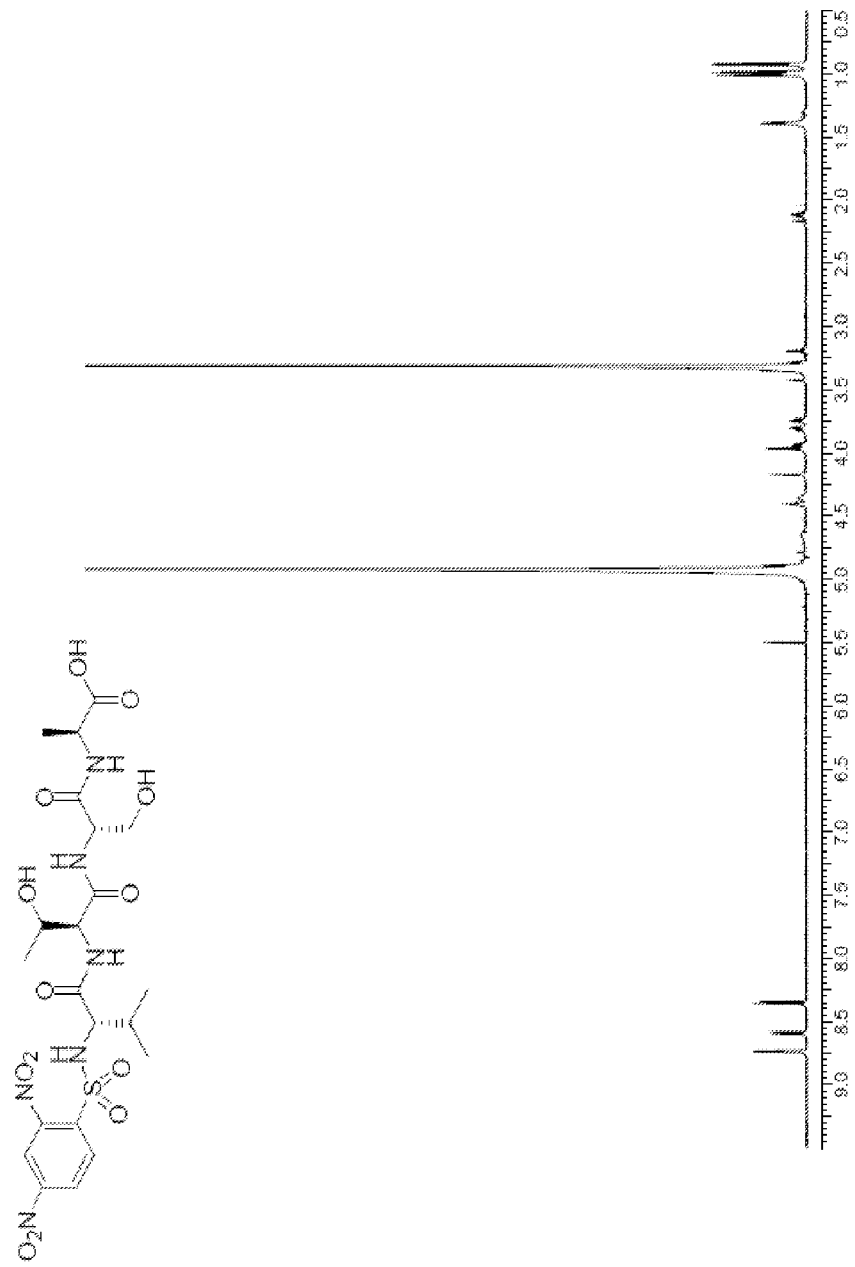
Figure 5. 1H NMR of dNBS-Val-Thr-Ser-Ala-OH (3).

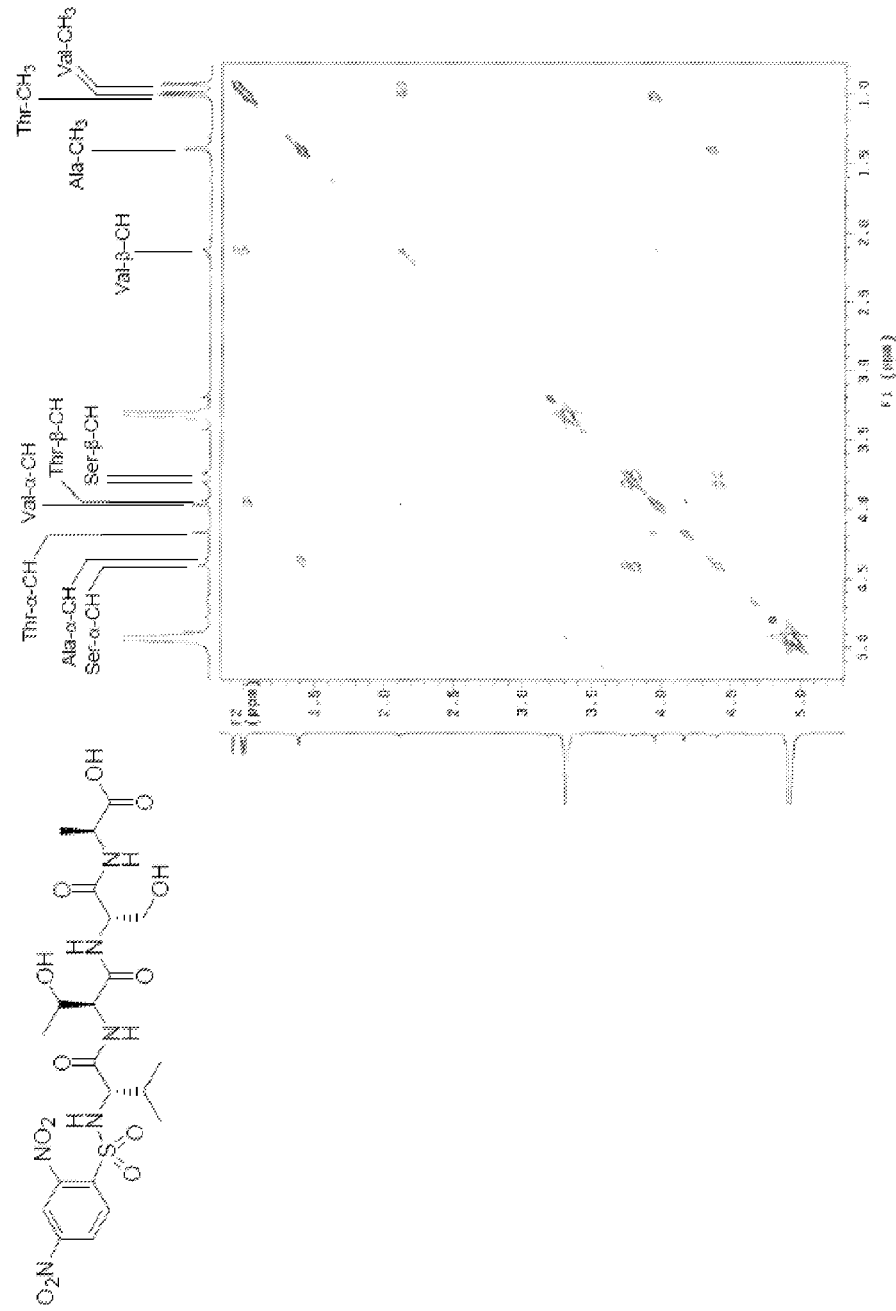
Figure 6. Characteristic region of $^1H$-$^1H$ gCOSY NMR of dNBS-Val-Thr-Ser-Ala-OH (3).

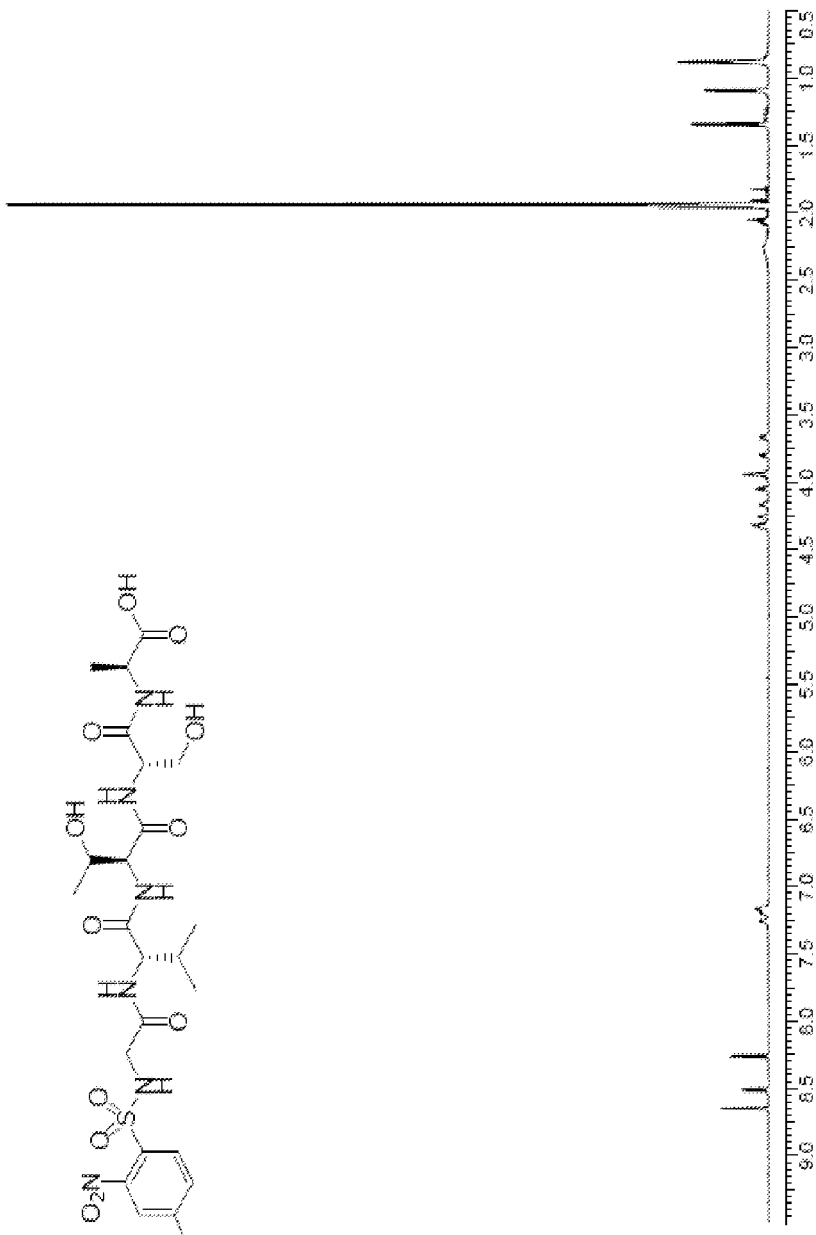
Figure 7. 1H NMR of dNBS-Gly-Val-Thr-Ser-Ala-OH (4).

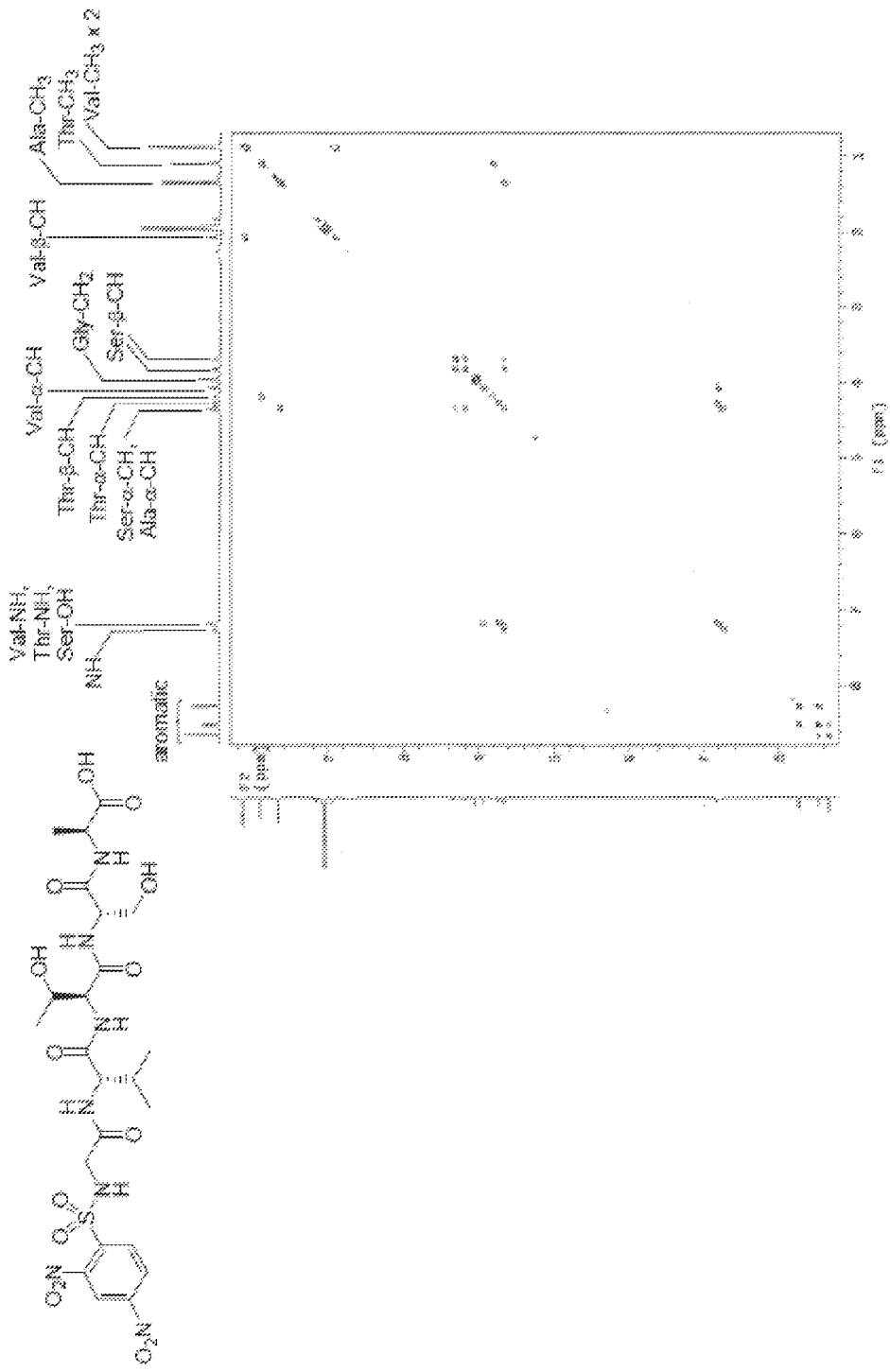
Figure 8. 1H-1H gCOSY NMR of dNBS-Gly-Val-Thr-Ser-Ala-OH (4).

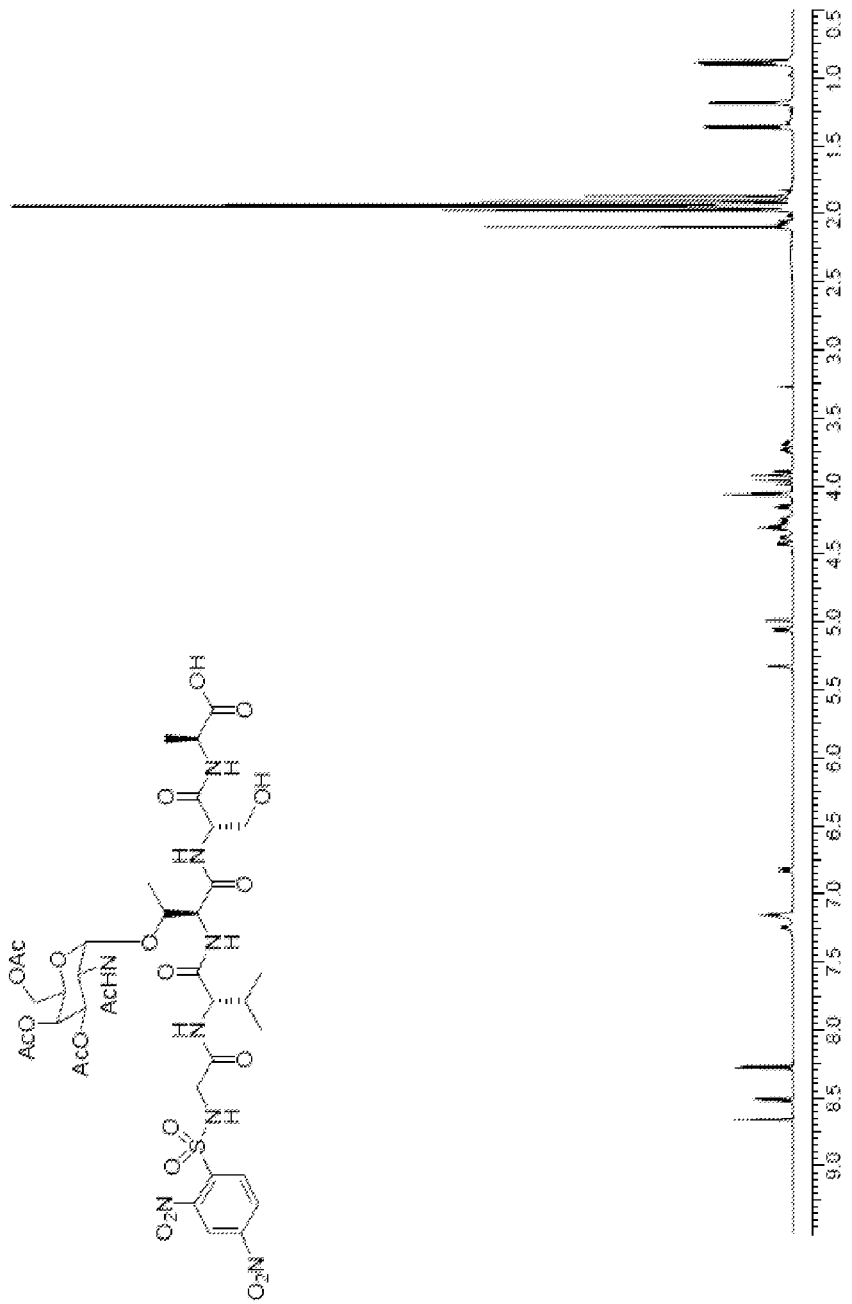
Figure 9. $^1$H NMR of dNBS-Gly-Val-(Ac$_3$-Tn-α-Thr)-Ser-Ala-OH (5).

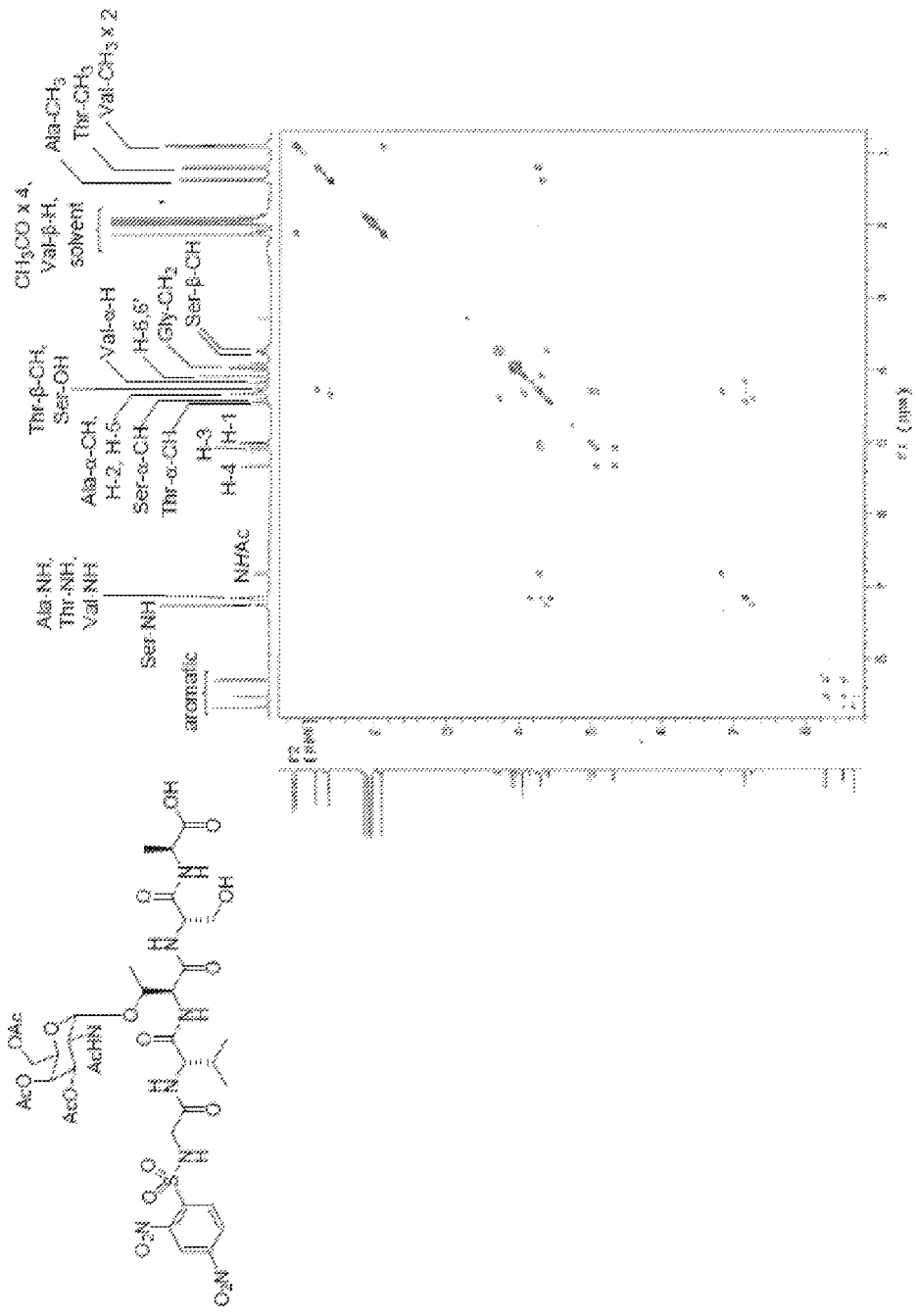

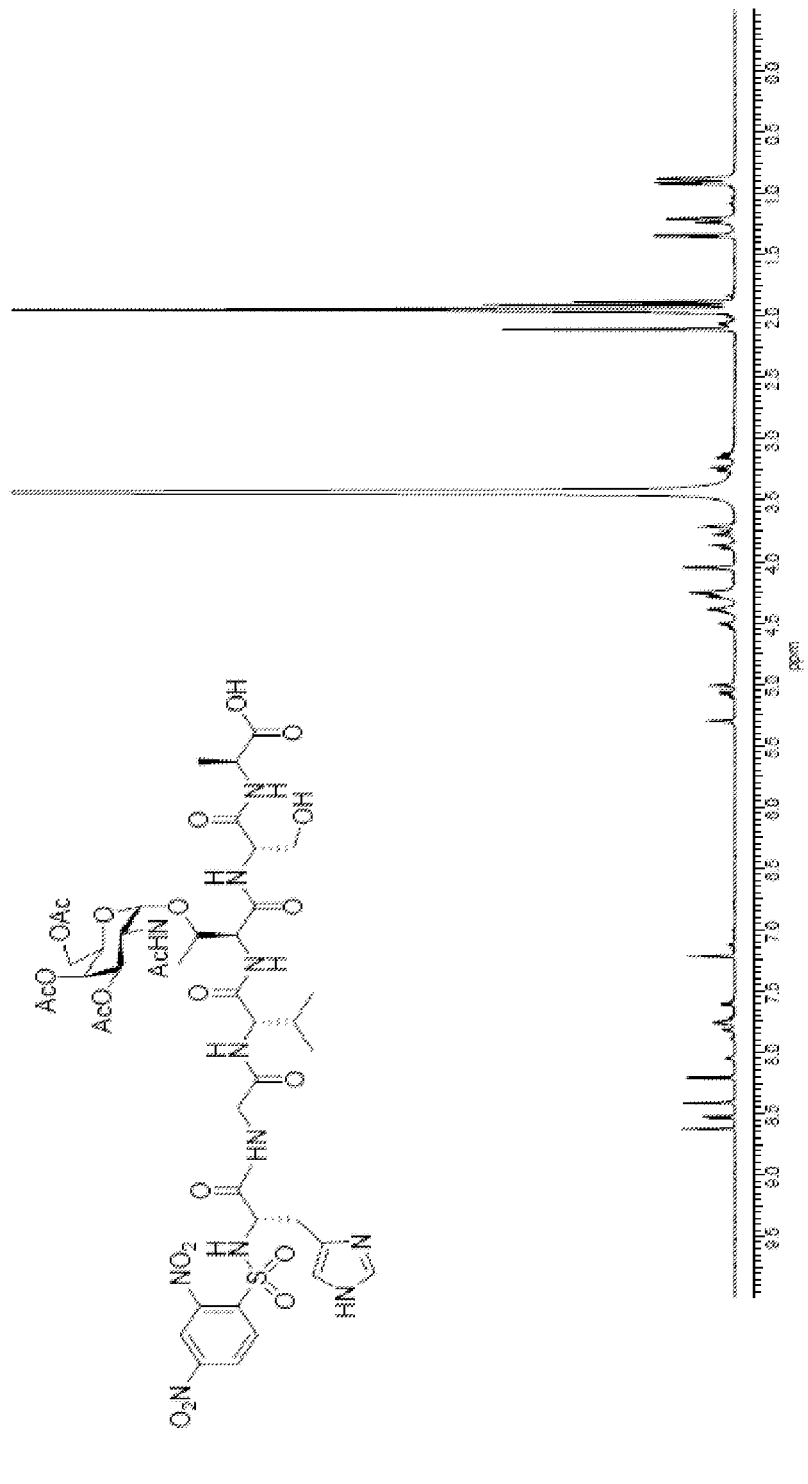
Figure 11. ¹H NMR of dNBS-His-Gly-Val-(Ac₃-Tn-α-Thr)-Ser-Ala-OH (6).

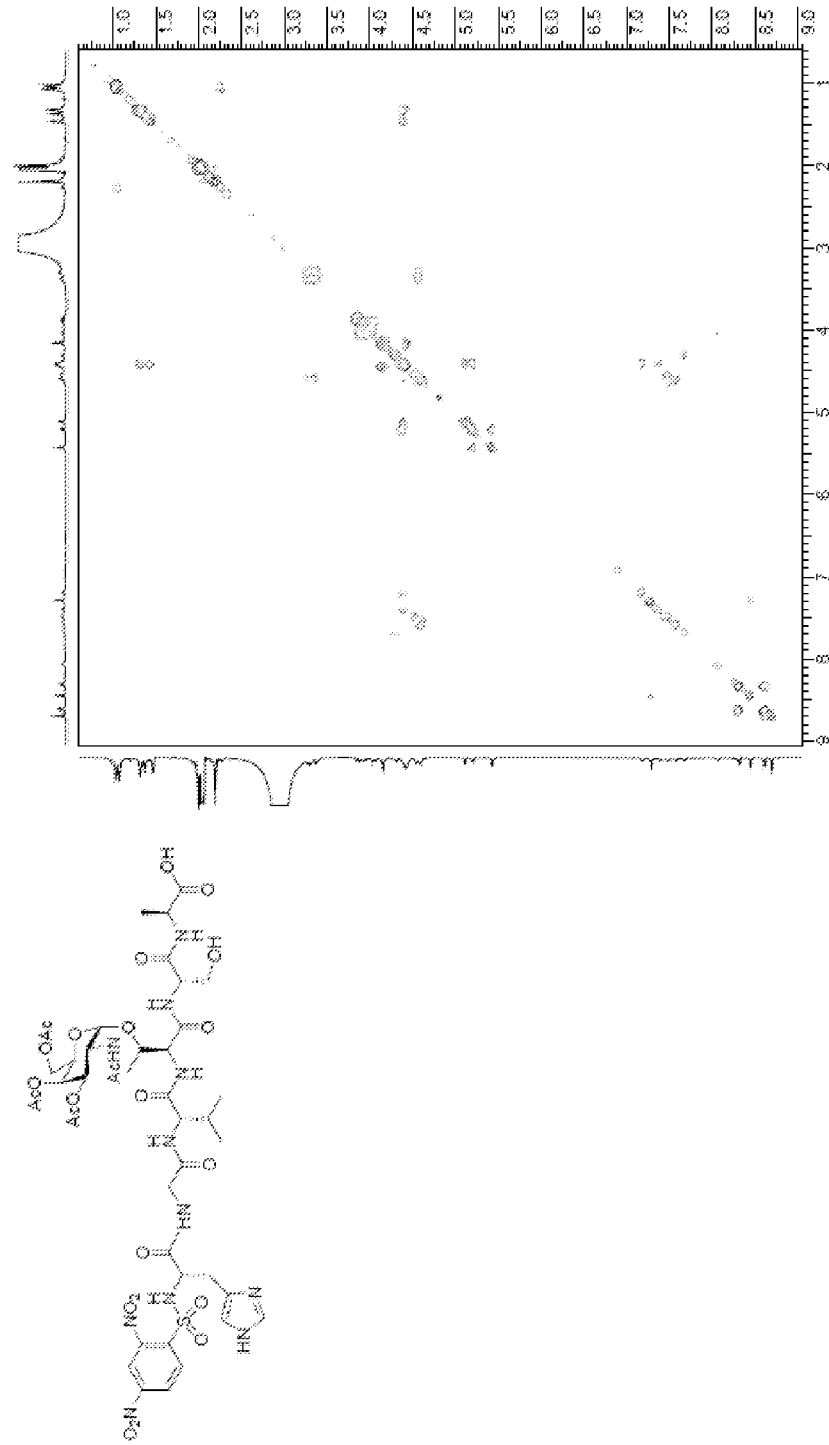
Figure 12. ¹H-¹H gCOSY NMR of dNBS-His-Gly-Val-(Ac₃-Tn-α-Thr)-Ser-Ala-OH (6).

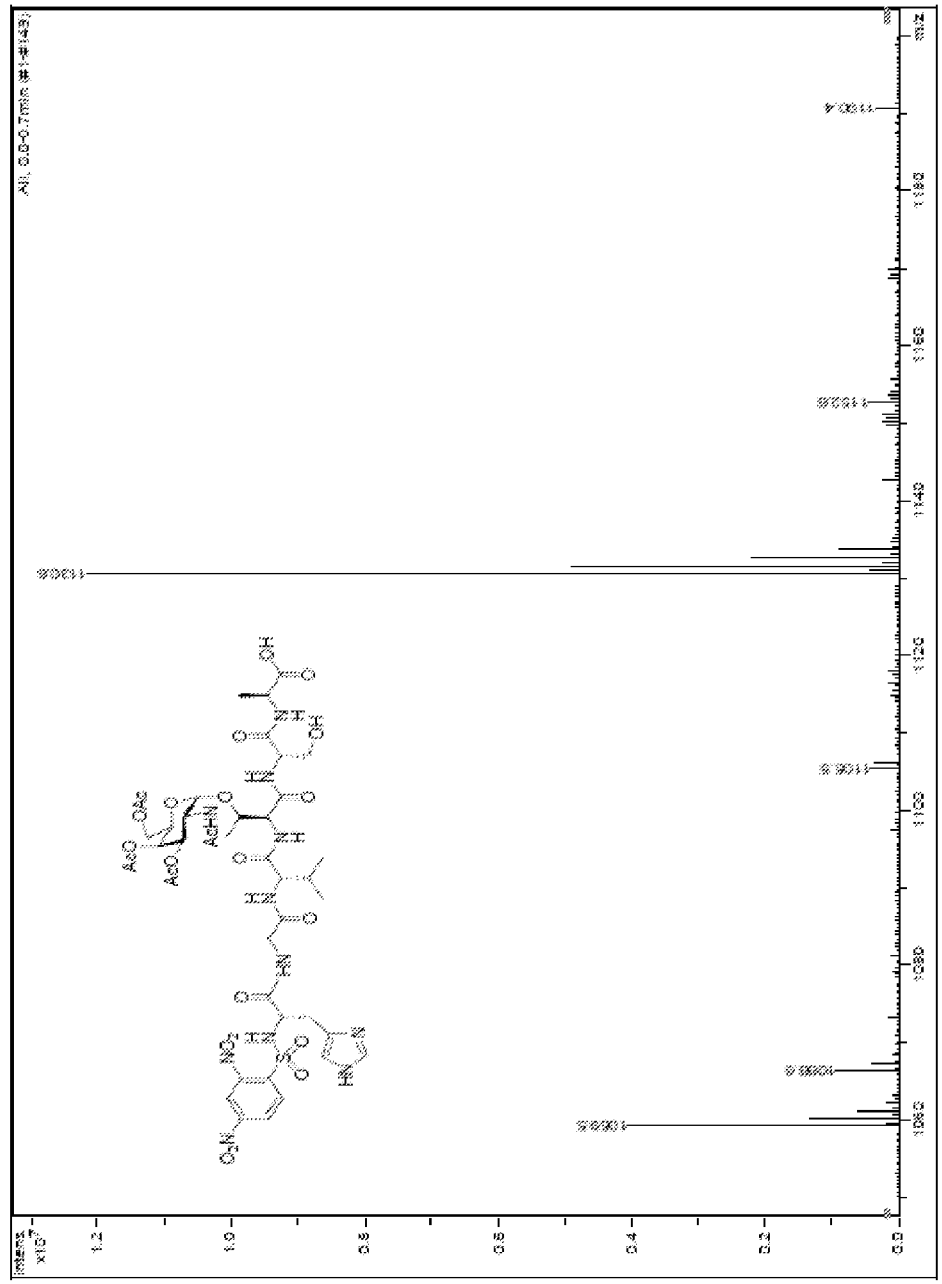
Figure 13. ESI-MS of dNBS-His-Gly-Val-(Ac₃-Tn-α-Thr)-Ser-Ala-OH (6).

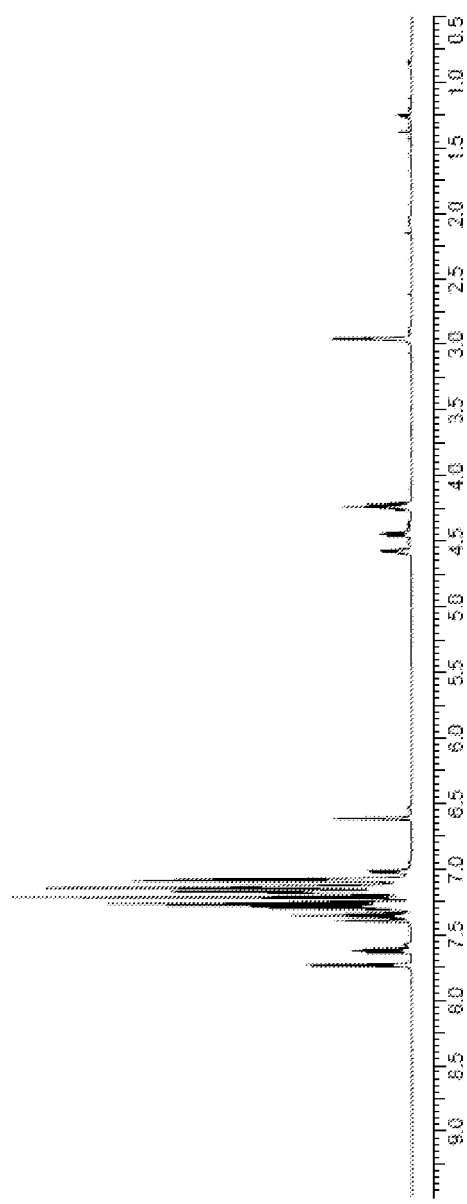
Figure 14. ¹H NMR of N-α-Fmoc-N-im-Trityl-Protected L-Histidine Trityl Thioester (7):

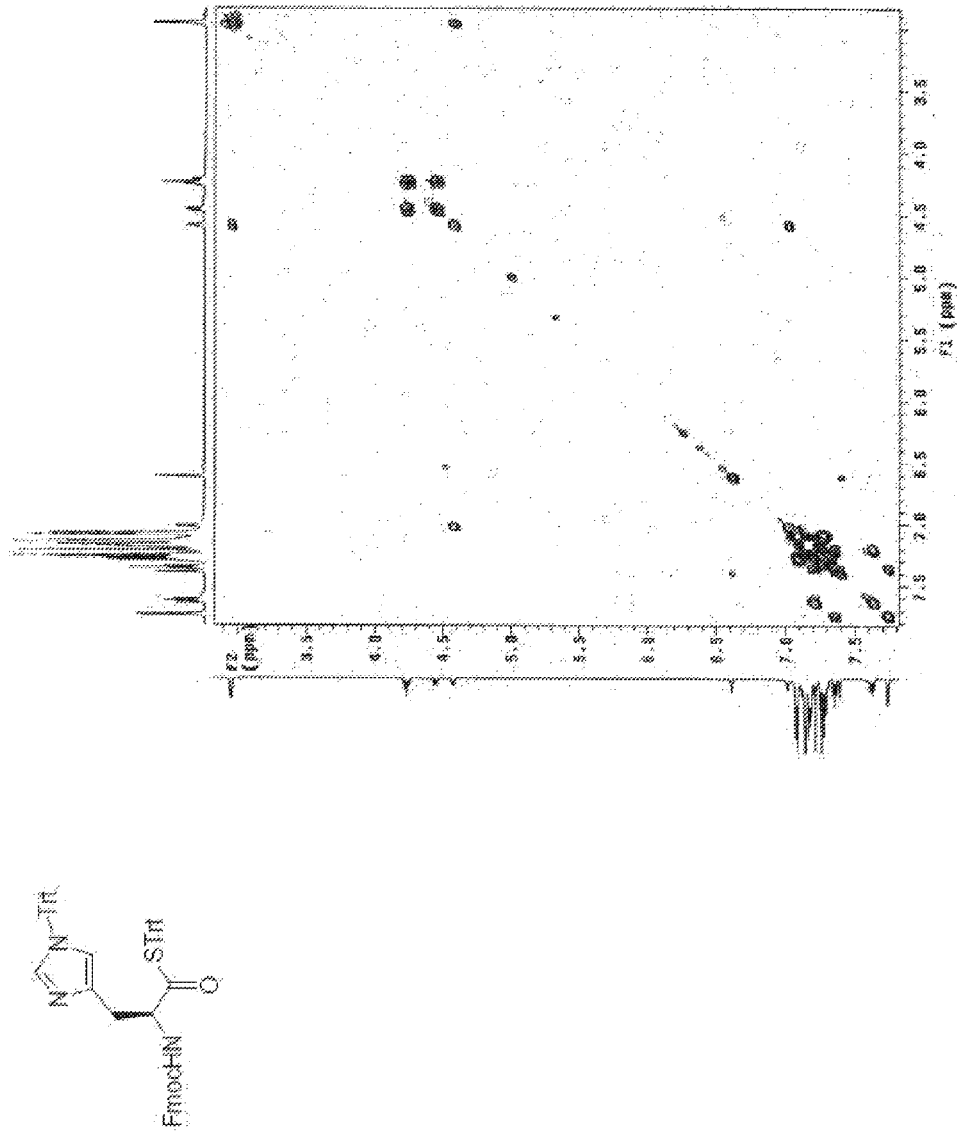
Figure 15. 1H-1H gCOSY NMR of N-α-Fmoc-N-im-Trityl-Protected L-Histidine Trityl Thioester (7).

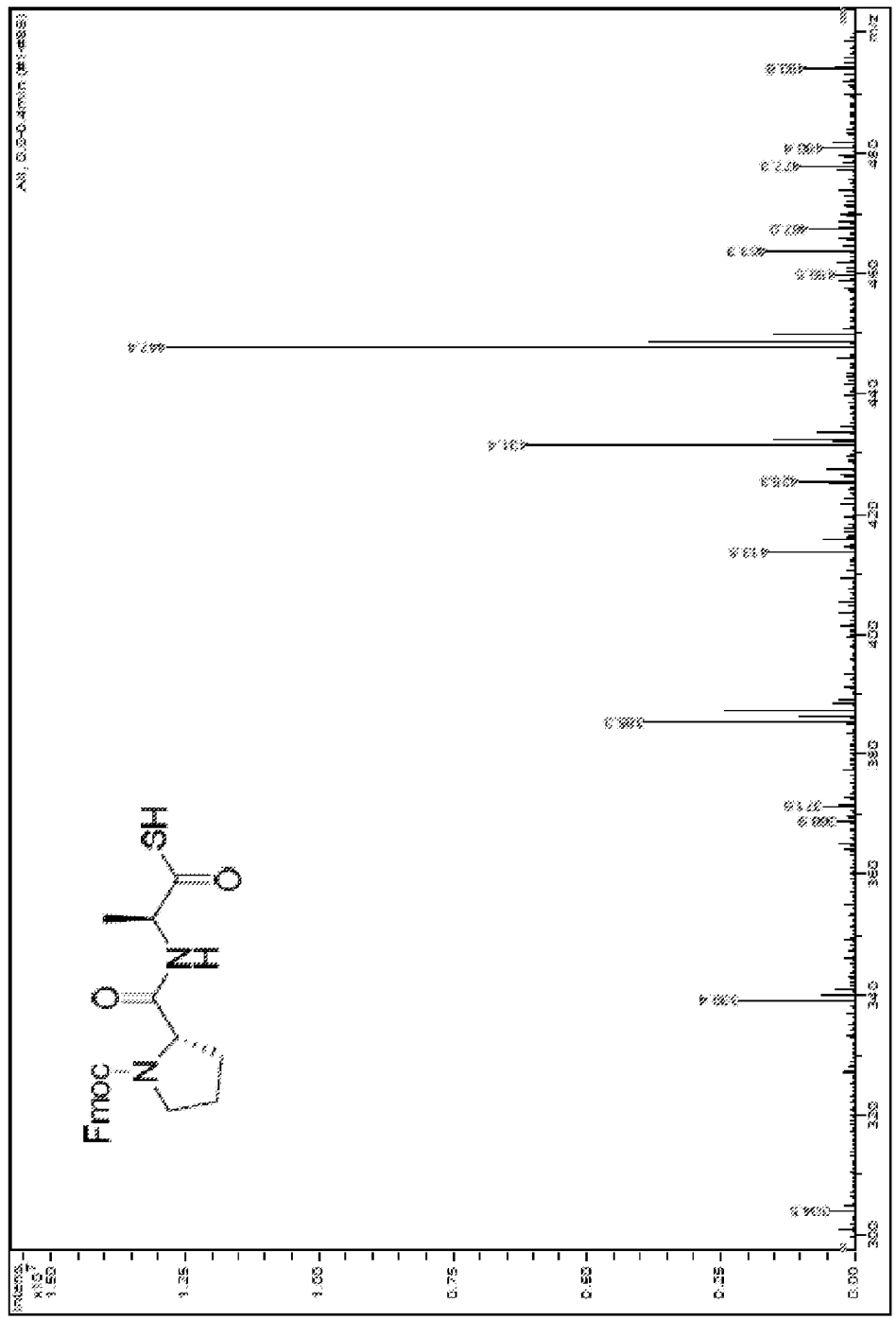
Figure 16. ESI-MS of Fmoc-Pro-Ala-SH (10).

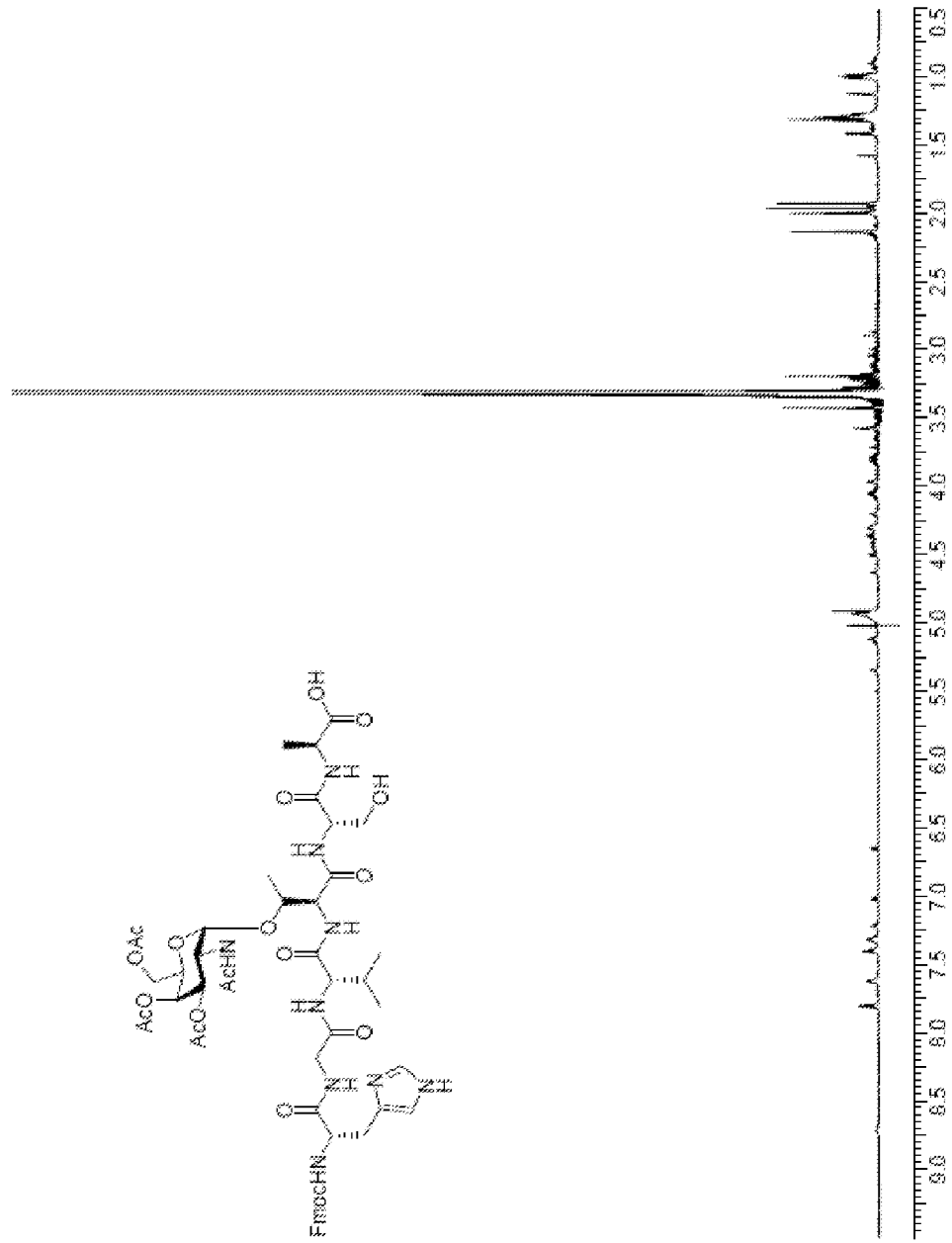
Figure 17. 1H NMR of N-Fmoc-His-Gly-Val(Ac3-Tn-α-Thr)-Ser-Ala-OH (11).

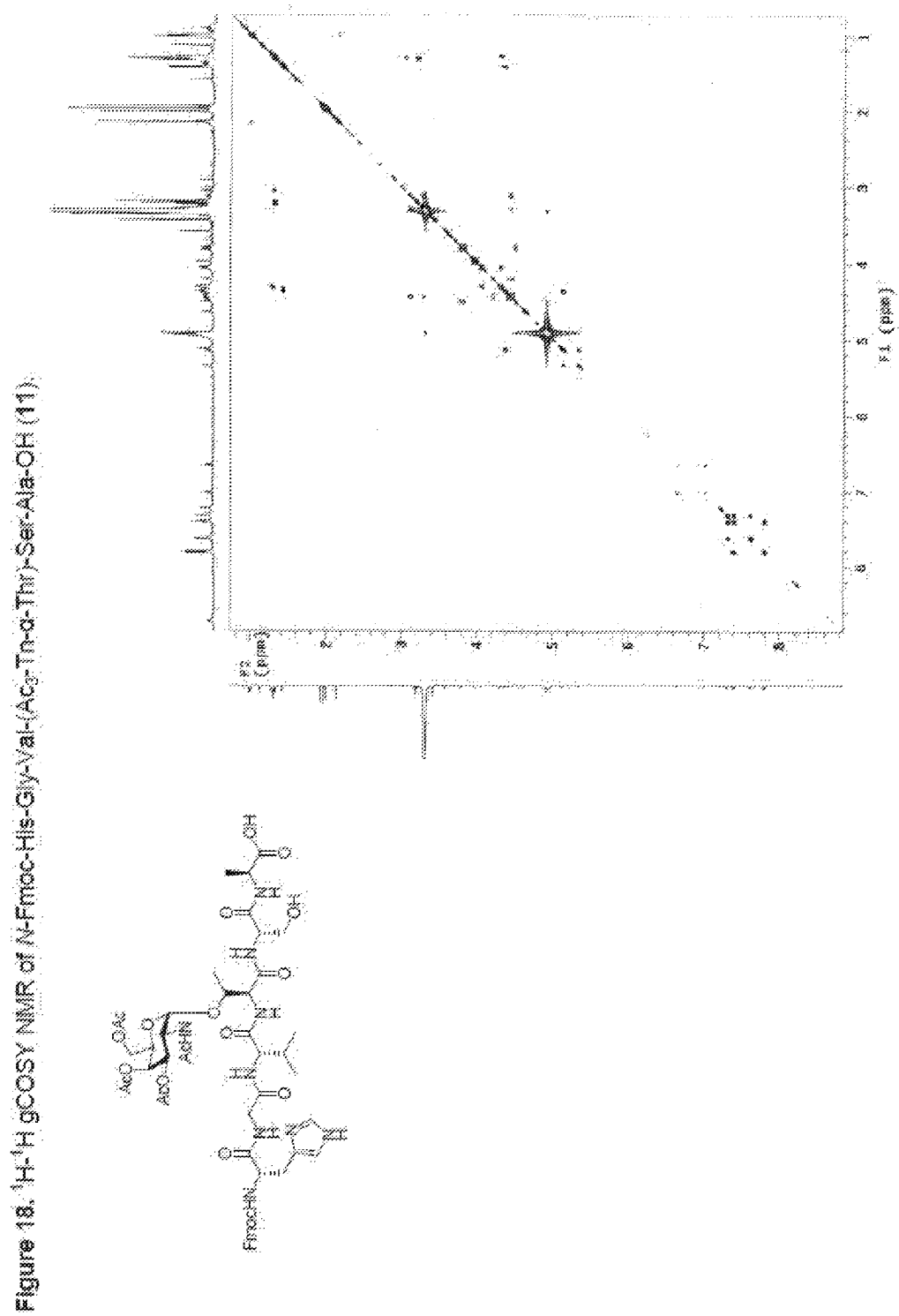
Figure 18. 1H-1H gCOSY NMR of N-Fmoc-His-Gly-Val-(Ac₃-Tn-α-Thr)-Ser-Ala-OH (11).

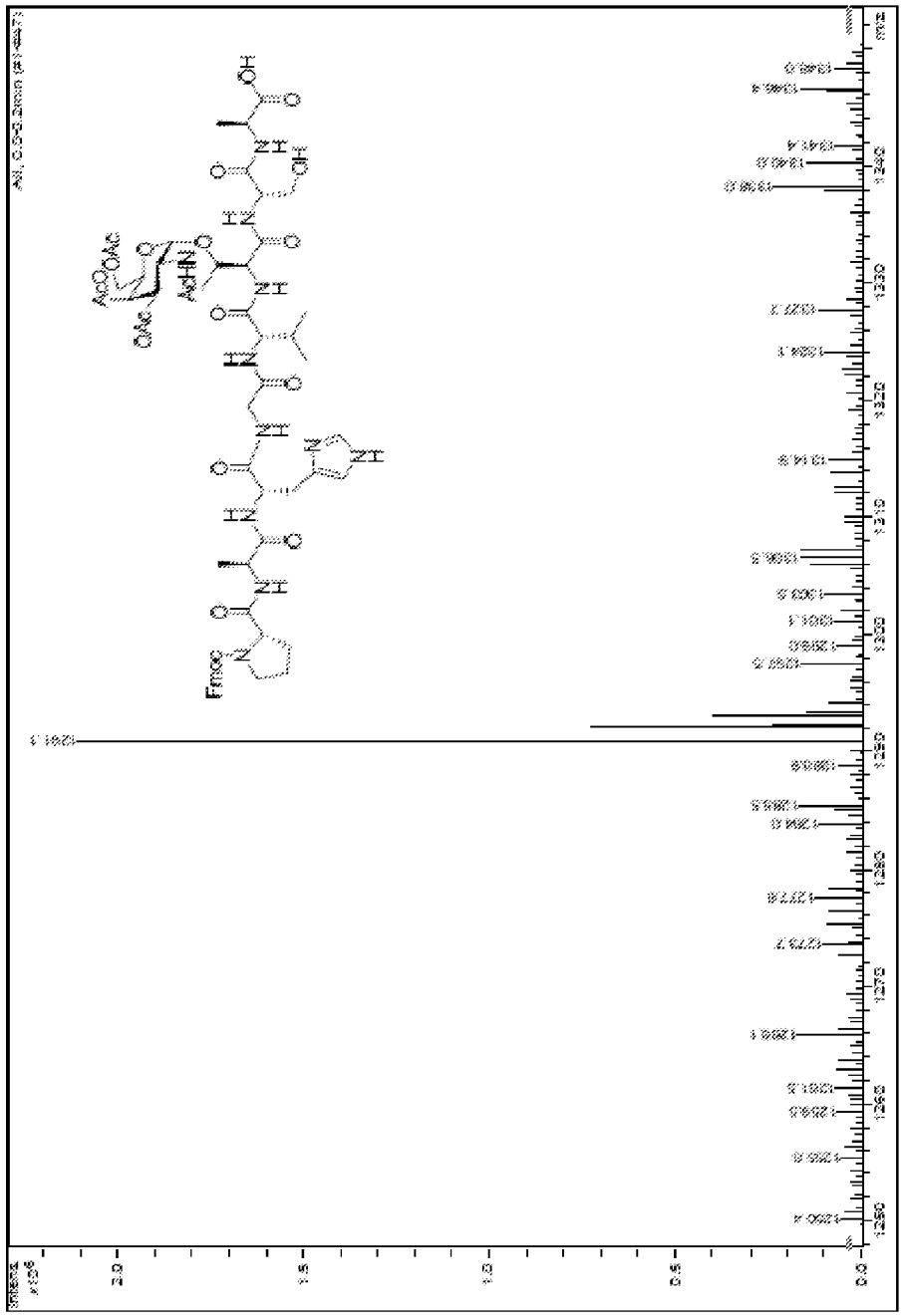
Figure 19. ESI-MS of Fmoc-Pro-Ala-His-Gly-Val-(Ac₃-Tn-α-Thr)-Ser-Ala-OH (12).

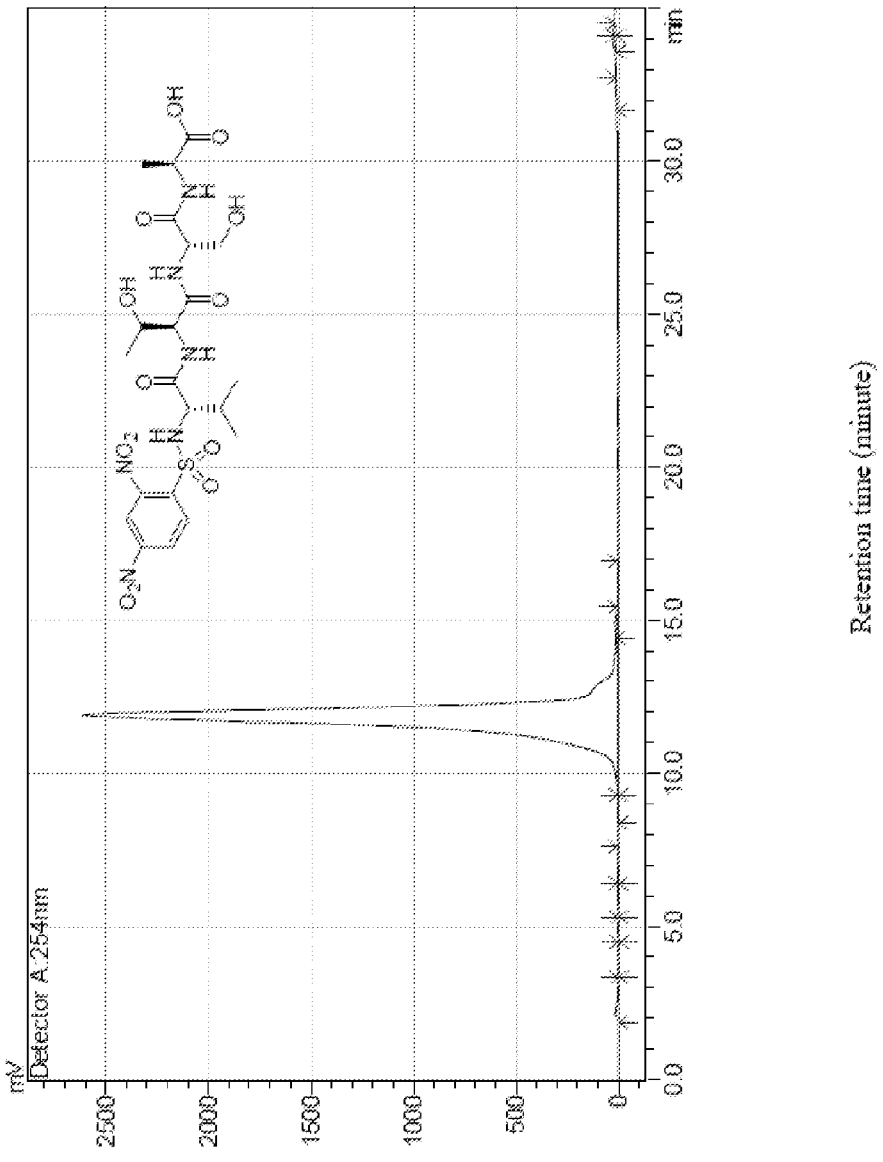
Figure 20. Analytical RP-HPLC of purified dNBS-Val-Thr-Ser-Ala-OH (3) eluting with 35-90% gradient of H₂O (0.1% TFA) and MeOH (0.1% TFA) over a period of 35 minutes. UV detection at 254 nm.

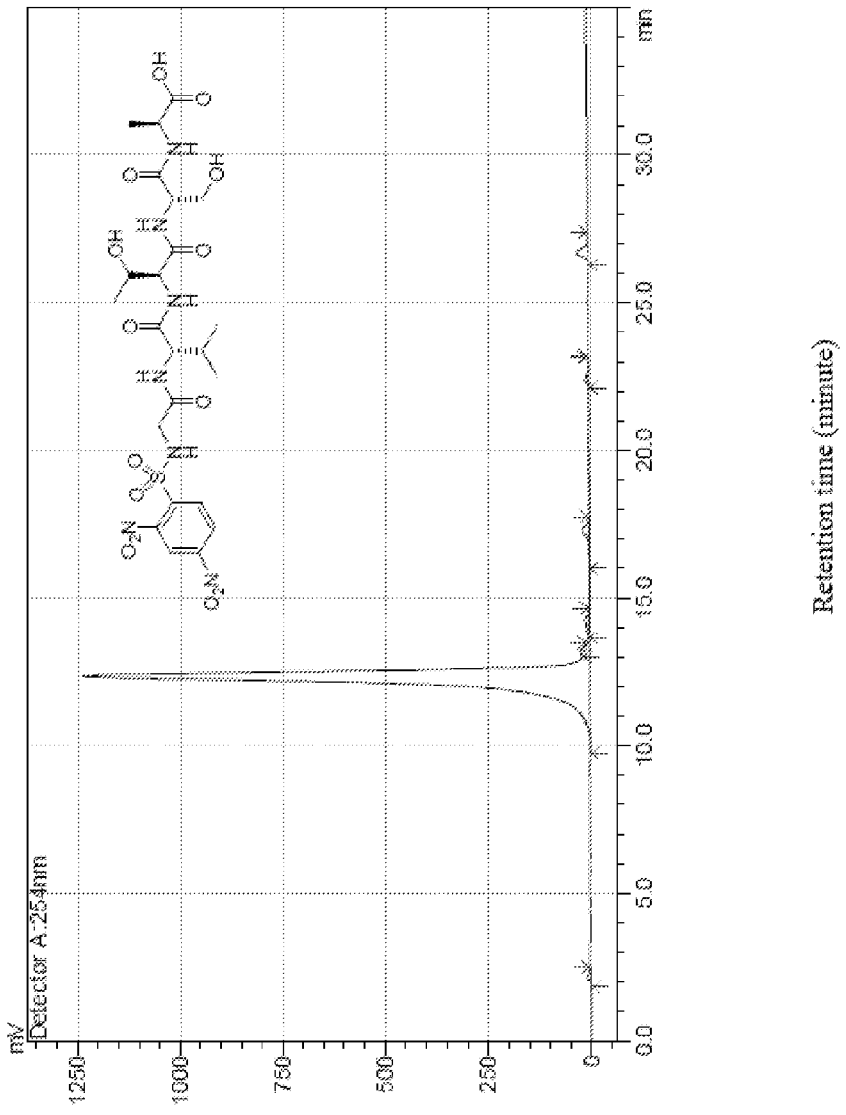
Figure 21. Analytical RP-HPLC of purified dNBS-Gly-Val-Thr-Ser-Ala-OH (4) eluting with 30-90% gradient of H₂O (0.1%TFA) and MeOH (0.1% TFA) over a period of 35 minutes, UV detection at 254 nm.

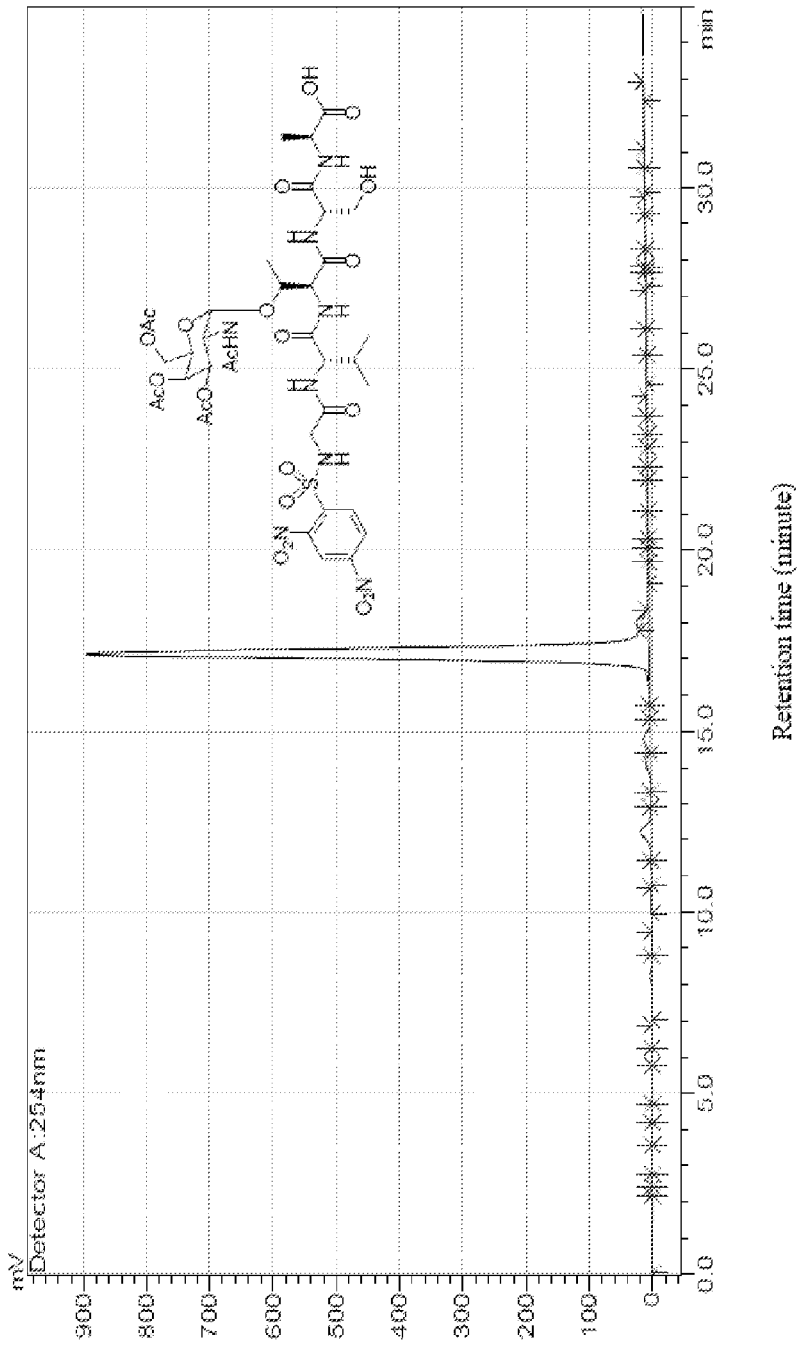
Figure 22. Analytical RP-HPLC of purified and dNBS-Gly-Val-(Ac₃-Tn-α-Thr)-Ser-Ala-OH (5) eluting with 30-90% gradient of H₂O (0.1%TFA) and MeOH (0.1% TFA) over a period of 35 minutes. UV detection at 254 nm.

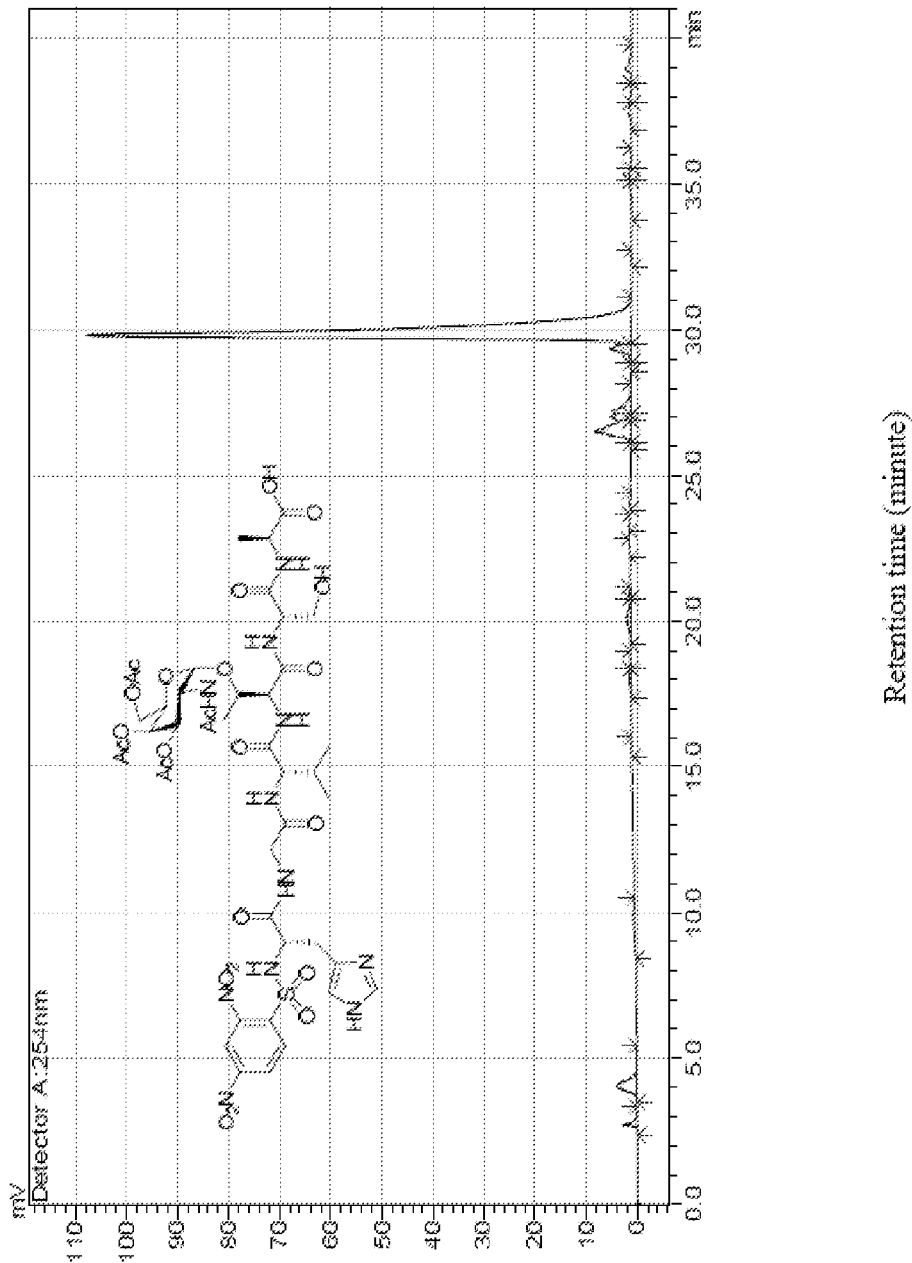
Figure 23. Analytical RP-HPLC of purified dNBS-His-Gly-Val-(Ac$_3$-Tn-α-Thr)-Ser-Ala-OH (6), eluting with 3-55% gradient of H$_2$O (0.1%TFA) and ACN over a period of 50 minutes, UV detection at 254 nm.

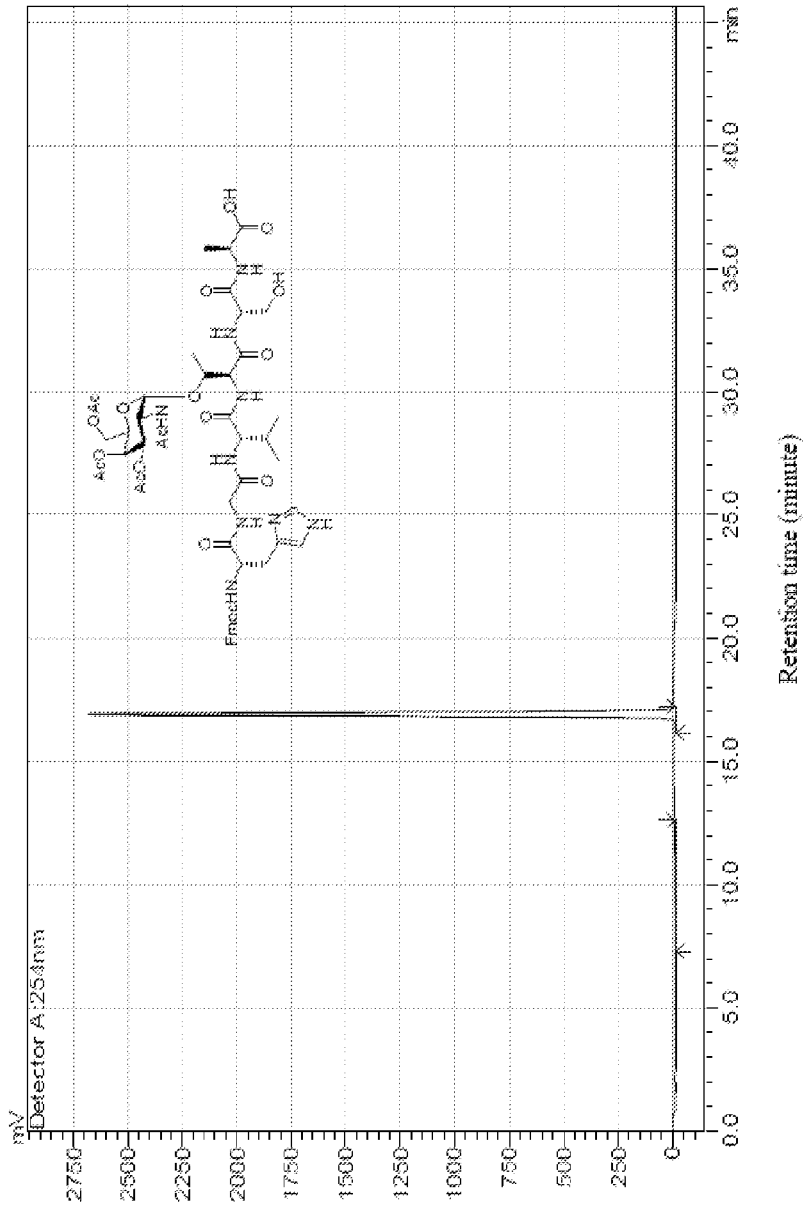
Figure 24. Analytical RP-HPLC of purified Fmoc-His-Gly-Val-(Ac₃-Tn-α-Thr)-Ser-Ala-OH (11), eluting with 30-90% gradient of H₂O (0.1% TFA) and MeOH (0.1% TFA) over a period of 35 minutes. UV detection at 254 nm.

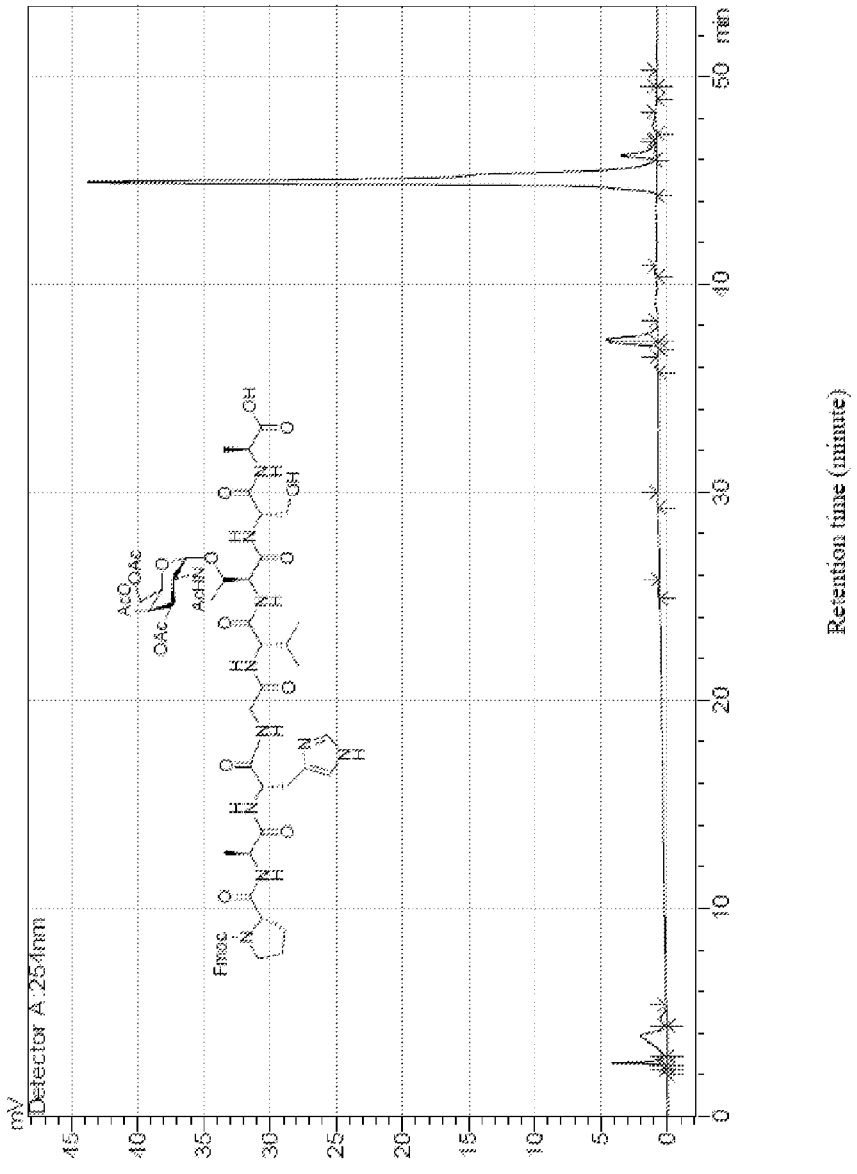
Figure 25. Analytical RP-HPLC of purified Fmoc-Pro-Ala-His-Gly-Val-(Ac₃-Tn-α-Thr)-Ser-Ala-OH (12), eluting with 3-55% gradient of H₂O (0.1% TFA) and ACN over a period of 50 minutes. UV detection at 254 nm.

Scheme 1. The Reaction of Sulfonamides and Thioacids to Form Amides.

Scheme 2. A General Strategy for the Synthesis of N-Peptidylsulfonamides

Scheme: 3. General strategy for mixed phase synthesis of peptide sequences

FIG. 29

Scheme 4

METHODS FOR FORMING PEPTIDES AND PEPTIDE CONJUGATES AND PEPTIDES AND PEPTIDE CONJUGATES COMPOSITIONS FORMED THEREBY

CROSS-REFERENCE TO RELATED APPLICATIONS

The present application claims the benefit of U.S. provisional patent application 61/529,435, filed on Aug. 31, 2011, the contents of which are hereby incorporated by reference in their entirety.

TECHNICAL FIELD AND INDUSTRIAL APPLICABILITY OF THE INVENTION

The invention generally relates to the field of solid-phase peptide synthesis, and in particular to improved methods for building peptide chains by attaching amino acids (such as Fmoc- and Alloc-protected amino acids) to a growing peptide using a solid-phase peptide synthesis process. The method includes building peptide chains containing sulfonyl modified amines either: i) at the N-terminus of the growing peptide; or, ii) within an amino acid side chain of the growing peptide. The invention also generally relates to the peptides and the peptide conjugates formed by the methods described herein.

BACKGROUND OF THE INVENTION

The solid-phase peptide synthesis (SPPS) of biologically active peptides, glycopeptides and glycoconjugates is a field of great interest. While SPPS is generally a mature technology, there is still an urgent need for improved methods to synthesize "difficult" peptides and peptide conjugates. Various peptides and/or conjugates are considered "difficult" when the synthesis of the peptide sequences results in incomplete peptide bond formation and/or when deprotection reactions occur at various stages in the SPPS.

These synthesizing problems can result from steric effects when one or both amino acid units at the newly formed amide bond are bulky or possess β-branched side chains such as valine, isoleucine, threonine. Similarly, the problems can occur at glycosyl amino acids which are found in glycopeptides.

These problems occur with most of the common peptide coupling reagents and are more pronounced in solid-phase peptide synthesis due to the steric requirements of the resins used in the synthetic process. Attempts to overcome these problems include the use of larger molar equivalents of peptide coupling reagents and amino acids, or the use of repeated cycles of coupling, washing and recoupling. However, the use of additional reagents and time increases the cost of materials and the time required to complete the synthesis.

Other attempts to synthesize difficult or long peptides include the use of a mixed-phase synthesis process. A mixed phase synthesis includes the production of peptide fragments through solid-phase peptide synthesis, followed by an assembly of these fragments in solution. However, if the peptide coupling is not complete, either on the solid phase or in solution, then closely related peptide-based impurities will be introduced into the peptide synthesis process. This is of special concern since peptides of very high purity (>95 area-% by HPLC) are often required for use in medical applications. In addition, removing these closely related impurities can be difficult or impossible. Also, the additional purification effort adds to the cost of the overall peptide synthesis.

As one example of a difficult synthetic process, as described by Krüger, et al. (*Eur. J. Org. Chem.* 2008, 35, 5936-5945, in the linear solid-phase synthesis of a 31-mer peptide being investigated for the treatment of diabetes, fifteen (15) coupling steps were needed due to incomplete coupling. Further, the unreacted terminal amino groups that were formed had to be capped by acetylation.

As a consequence, others have used a mixed-phase synthesis as a strategy to deal with the difficult sequences in SPPS. In fact, currently, most large scale peptide syntheses of peptides longer than five amino acids are generally manufactured by a mixed or a convergent strategy (i.e., synthesis of small segments or fragments that are subsequently joined to give the final sequence). The mixed strategy, being convergent in nature, consumes less raw materials and reagents. Still, the overall yield of a synthesis becomes critical when considering that many pharmaceutically related peptides must be prepared on a multi-ton scale. Thus, there is an ongoing search for and selection of new starting reagents that enable the production of peptides faster, in a safer way, and at lower costs (Riniker, et al. *Tetrahedron* 1993, 49, 9307-9320; Barlos, et al. *Liebigs Ann. Chem. Ann. Chem.* 1993, 215-220; Bray *Nat. Rev. Drug Discovery* 2003, 2, 587-593; Andersson, et al. *Biopolymers* 2000, 55, 227-250; Bruckdorfer, et al. *Curr. Pharm. Biotechnol.* 2004, 5, 29-43).

Another technology to deal with difficult peptide synthesis is microwave irradiation during peptide synthesis (Coin, et al. *Nature Protocols,* 2007, 2, 3247-3256).

Still another technology includes the use of fluorous tag reagents which allow for solution phase synthesis and solid phase extraction of fluorous tag (Chen and Zhang, *Organic Letters* 2003, 5, 1015; Marshall and Liener, *J. Org. Chem.* 1970, 35, 867; Curran, D. P. *Synlett* 2001, 1488). The latter offers advantages common to solution phase chemistry and maintains the rapid nature of solid phase supports (Zhang, ACS Symposium Series 949, 2007, 207-220).

In addition to synthesizing peptides, there is a need to synthesize a variety of peptide conjugates. The purpose of creating a peptide conjugate can be manifold. One of the most well recognized and medicinally important types of peptide conjugate include PEGylated peptides and proteins. PEGylation is the practice of covalently coupling of poly(ethylene glycol) by the use of a PEGylation reagent to pharmaceutical proteins and peptides to improve their pharmacological properties. The original method was described by Davis and Abuchowski in the 1970s (Abuchowski et al. *J. Biol. Chem.* 1977, 252, 3582-3586). PEGylation has become the dominant protein/peptide-based drug delivery system for the biotech industry, with sales of PEGylated peptide and protein-based drugs reaching over $4 billion (Maggon, in *Handbook of Pharmaceutical and Biotechnology*, "R&D paradigm shift and billion-dollar biologics", John Wiley, 2007, pp. 161-198). Brocchini et al. (*Adv. Drug Delivery Rev.* 2008, 60, 4-13) noted that one of the key issues facing the field of PEGylation is the need to obtain site-specific peptide or protein PEGylation to avoid the loss of biological activity. It has also been noted that the desirable properties of PEGylation are not exclusive for poly(ethylene glycol) (Veronese *Adv. Drug Delivery Rev.* 2008, 60, 1-2).

For example, polymers of origin such as polysaccharides (Gregoriadis, et al. *Int. J. Pharm.* 2005, 300, 125-130; Fernandes, et al. *Int. J. Pharm.* 2001, 217, 215-224) and synthetic polymers (Veronese, et al., in: M. J. Harris, S. Zalipski (Eds.), Poly(ethylene glycol) Chemistry and Biological Applications, ACS Symposium Series, vol. 680, 1977, pp. 182-192; Miyamoto, et al., *Macromolecules* 1990, 23, 3201-3205; Gaertner, et al. *J. Control. Release* 2007, 119, 291-300) have demonstrated that molecules other than poly (ethylene glycol) can favorably modify protein and peptide properties.

To address both the need for new methods for difficult peptide synthesis and the need for site specific peptide and protein conjugation methods, new amide bond forming reactions are being researched. One proposed method included the reaction of thioacids with 2,4-dinitrobenzenesulfonamides (dNBSs). Originally, the dNBS group was used as a protecting group for the alkylation of primary amines (Fukuyama, et al. *Tetrahedron Lett.* 1997, 38, 5831-5834).

The dNBS group as a N-sulfonamide derivative 1 (FIG. 26—PRIOR ART Scheme 1) was later found to facilitate the formation of amides 3 in the presence of thioacids (Messeri, et al. *Tetrahedron Lett.* 1998, 39, 1669-1672; Messeri, et al. *Tetrahedron Lett.* 1998, 39, 1673-1676). The mechanism involves ipso attack of the thioacid on the sulfonamide to form a Meisenheimer complex 2. The nitrogen of the sulfonamide ultimately attacks the adjacent thioester with extrusion of SO2. The chemistry has been shown to be amenable to the coupling of hindered amino acid derivatives to form native peptide fragments and peptide conjugates (Crich, et al. *Org. Lett.* 2007, 9, 4423-4426, Crich, et al. *Org. Lett.* 2007, 9, 5323-5325).

In addition the β-N-dNBS-glycosylsulfonamides have been shown to provide β-configured glycosyl amino acids common to most N-linked glycopeptides/proteins when reacted with amino thioacids (Talan et al. *Carbohydr. Res.* 2009, 344: 2048-2050). The reaction between dNBS-modified amines and thioacids can be performed at room temperature and is complete in thirty minutes. The observed yields of this ligation are comparable with other methods such as the Staudinger ligation reaction (Doores et al. *Chem. Comm.* 2006, 1401-1403; He et al. *Org. Lett.* 2004, 6, 4479-4482; Györgydeák, et al. *Bioorg. Med. Chem.* 2004, 12, 4861-4870).

Aside from the efficient chemistry underlying a given amide bond forming reaction, its adoption depends on the straightforward synthesis of the requisite fragments to be coupled. Some, N-peptidyl arylsulfonamides have been reported to be amenable to SPPS synthesis. For example, ortho-nitrobenzenesulfonamides (o-NBS) and paranitrobenzenesulfonamides (p-NBS) have been coupled to the N-terminus of a peptide bound to Rink amide 4-methylbenzhydrylamine (MBHA) resin (Miller, et al. *J. Am. Chem. Soc.* 1997, 119, 2301-2302) while o-NBS-amino acids have been synthesized off-resin and used in SPPS (Miller, et al. *J. Am. Chem. Soc.* 1998, 120, 2690-2691). In both instances, the N-arylsufonyl group was used as protecting group to aid in the controlled alkylation of the N-terminus, and was removed afterwards.

Consequently, there is a need in the field of peptide synthesis and peptide conjugate synthesis for chemistry capable linking sterically demanding amino acids to form difficult peptides.

Furthermore, there is a need for linking chemistry that can facilitate the sitespecific conjugation of an untold number of compounds to peptides and proteins, in particular PEGylating reagents, polymers, and saccharides.

Despite the diverse methods describe above, there is still a need in the field of peptide synthesis and peptide conjugate synthesis for a synthetic method that is capable of linking sterically demanding amino acids to form difficult peptides.

Furthermore, there is a need for a synthetic method that can facilitate the site-specific conjugation of one or more types of desired compounds to peptides and proteins, such as, in particular PEGylating reagents, polymers, and saccharides.

The inventors herein have now greatly improved upon previous methods for peptide synthesis.

SUMMARY OF THE INVENTION

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The present invention is based, at least in part, on the inventors' discovery of a method that is capable of linking sterically demanding amino acids to form difficult peptides.

In a first broad aspect, described herein is a method for the solid-phase peptide synthesis of "difficult" peptides and peptide conjugates.

One method described herein allows the installation of the dNBS group or other sulfonamide directly to the N-terminus of a growing peptide on a resin or a fluorous tag without the need to synthesize dNBS or other sulfonamide-modified amino acids or peptides.

The method also allows for the dNBS group or other sulfonamide to be attached site specifically to any position of an amino acid side chain during a SPPS. The dNBS group or other sulfonamide can remain intact through the cleavage step of the peptide from the resin in order to affect the desired amide bond formation reaction with a thioacid off-resin as is required in the case of mixed methods for peptide of peptide conjugate synthesis.

It is to be understood that the present invention is not limited to off-resin peptide formation or conjugation reactions and can be used for preparing dNBS- or other sulfonamide-modified peptides that can then be coupled with thioacids while the dNBS- or other sulfonamide-modified peptides remain attach to a resin or a fluorous tag.

In another broad aspect, the present invention includes the compounds derived when applying the methods described herein.

In one particular aspect, there is provided herein a method for building peptide chains by attaching amino acids (such as Fmoc- and Alloc-protected amino acids) to a growing peptide using a solid-phase peptide synthesis process. The method generally includes building peptide chains containing sulfonyl modified amines either: i) at the N-terminus of the growing peptide; or, ii) within an amino acid side chain of the growing peptide.

In another broad aspect, there is provided herein the peptides and the peptide conjugates formed by the methods described herein.

In another aspect, there is provided herein compositions having sulfonyl modified amines attached to the N-terminus or within amino acid sidechains of a polypeptide containing three or more amino acid residues.

Other systems, methods, features, and advantages of the present invention will be or will become apparent to one with skill in the art upon examination of the following drawings and detailed description. It is intended that all such additional systems, methods, features, and advantages be included within this description, be within the scope of the invention, and be protected by the accompanying claims.

BRIEF DESCRIPTION OF THE DRAWINGS

FIG. 1 is diagram showing: $^1$H NMR of dNBS-Alanine (1).

FIG. 2 is a diagram showing: $^{13}$C NMR of dNBS-Alanine (1).

FIG. 3 is a diagram showing: ¹H NMR of dNBS-Ser-Ala-OH (2).

FIG. 4 is a diagram showing: ¹H-¹H gCOSY NMR of dNBS-Ser-Ala-OH (2).

FIG. 5 is a diagram showing: ¹H NMR of dNBS-Val-Thr-Ser-Ala-OH (3) (SEQ ID NO: 1).

FIG. 6 is a diagram showing: Characteristic region of ¹H-¹H gCOSY NMR of dNBS-Val-Thr-Ser-Ala-OH (3) (SEQ ID NO: 1).

FIG. 7 is a diagram showing: ¹H NMR of dNBS-Gly-Val-Thr-Ser-Ala-OH (4) (SEQ ID NO: 2).

FIG. 8 is a diagram showing: ¹H-¹H gCOSY NMR of dNBS-Gly-Val-Thr-Ser-Ala-OH (4) (SEQ ID NO: 2).

FIG. 9 is a diagram showing: ¹H NMR of dNBS-Gly-Val-($Ac_3$-Tn-α-Thr)-Ser-Ala-OH (5) (SEQ ID NO: 3).

FIG. 10 is a diagram showing: ¹H-¹H gCOSY NMR of dNBS-Gly-Val-($Ac_3$-Tn-α-Thr)-Ser-Ala-OH (5) (SEQ ID NO: 3).

FIG. 11 is a diagram showing: ¹H NMR of dNBS-His-Gly-Val-($Ac_3$-Tn-α-Thr)-Ser-Ala-OH (6) (SEQ ID NO: 6).

FIG. 12 is a diagram showing: ¹H-¹H gCOSY NMR of dNBS-His-Gly-Val-($Ac_3$-Tn-α-Thr)-Ser-Ala-OH (6) (SEQ ID NO: 6).

FIG. 13 is a diagram showing: ESI-MS of dNBS-His-Gly-Val-($Ac_3$-Tn-α-Thr)-Ser-Ala-OH (6) (SEQ ID NO: 6).

FIG. 14 is a diagram showing: ¹H NMR of N-α-Fmoc-N-im-Trityl-Protected L-Histidine Trityl Thioester (7).

FIG. 15 is a diagram showing: ¹H-¹H gCOSY NMR of N-α-Fmoc-N-im-Trityl-Protected L-Histidine Trityl Thioester (7).

FIG. 16 is a diagram showing: ESI-MS of Fmoc-Pro-Ala-SH (10).

FIG. 17 is a diagram showing: ¹H NMR of N-Fmoc-His-Gly-Val-($Ac_3$-Tn-α-Thr)-Ser-Ala-OH (11) (SEQ ID NO: 4).

FIG. 18 is a diagram showing: ¹H-¹H gCOSY NMR of N-Fmoc-His-Gly-Val-($Ac_3$-Tn-α-Thr)-Ser-Ala-OH (11) (SEQ ID NO: 4).

FIG. 19 is a diagram showing: ESI-MS of Fmoc-Pro-Ala-His-Gly-Val-($Ac_3$-Tn-α-Thr)-Ser-Ala-OH (12) (SEQ ID NO: 5).

FIG. 20 is a diagram showing: Analytical RP-HPLC of purified dNBS-Val-Thr-Ser-Ala-OH (3) (SEQ ID NO: 1) eluting with 35-90% gradient of $H_2O$ (0.1% TFA) and MeOH (0.1% TFA) over a period of 35 minutes, UV detection at 254 nm.

FIG. 21 is a diagram showing: Analytical RP-HPLC of purified dNBS-Gly-Val-Thr-Ser-Ala-OH (4) (SEQ ID NO: 2) eluting with 30-90% gradient of $H_2O$ (0.1% TFA) and MeOH (0.1% TFA) over a period of 35 minutes, UV detection at 254 nm.

FIG. 22 is a diagram showing: Analytical RP-HPLC of purified and dNBS-Gly-Val-($Ac_3$-Tn-α-Thr)-Ser-Ala-OH (5) (SEQ ID NO: 3) eluting with 30-90% gradient of $H_2O$ (0.1% TFA) and MeOH (0.1% TFA) over a period of 35 minutes, UV detection at 254 nm.

FIG. 23 is a diagram showing: Analytical RP-HPLC of purified dNBS-His-Gly-Val-($Ac_3$-Tn-α-Thr)-Ser-Ala-OH (6) (SEQ ID NO: 6), eluting with 3-55% gradient of $H_2O$ (0.1% TFA) and ACN over a period of 50 minutes, UV detection at 254 nm.

FIG. 24 is a diagram showing: Analytical RP-HPLC of purified N-Fmoc-His-Gly-Val-($Ac_3$-Tn-α-Thr)-Ser-Ala-OH (11) (SEQ ID NO: 4), eluting with 30-90% gradient of $H_2O$ (0.1% TFA) and MeOH (0.1% TFA) over a period of 35 minutes, UV detection at 254 nm.

FIG. 25 is a diagram showing: Analytical RP-HPLC of purified Fmoc-Pro-Ala-His-Gly-Val-($Ac_3$-Tn-α-Thr)-Ser-Ala-OH (12) (SEQ ID NO: 5), eluting with 3-55% gradient of $H_2O$ (0.1% TFA) and ACN over a period of 50 minutes, UV detection at 254 nm.

PRIOR ART

Figure 29:
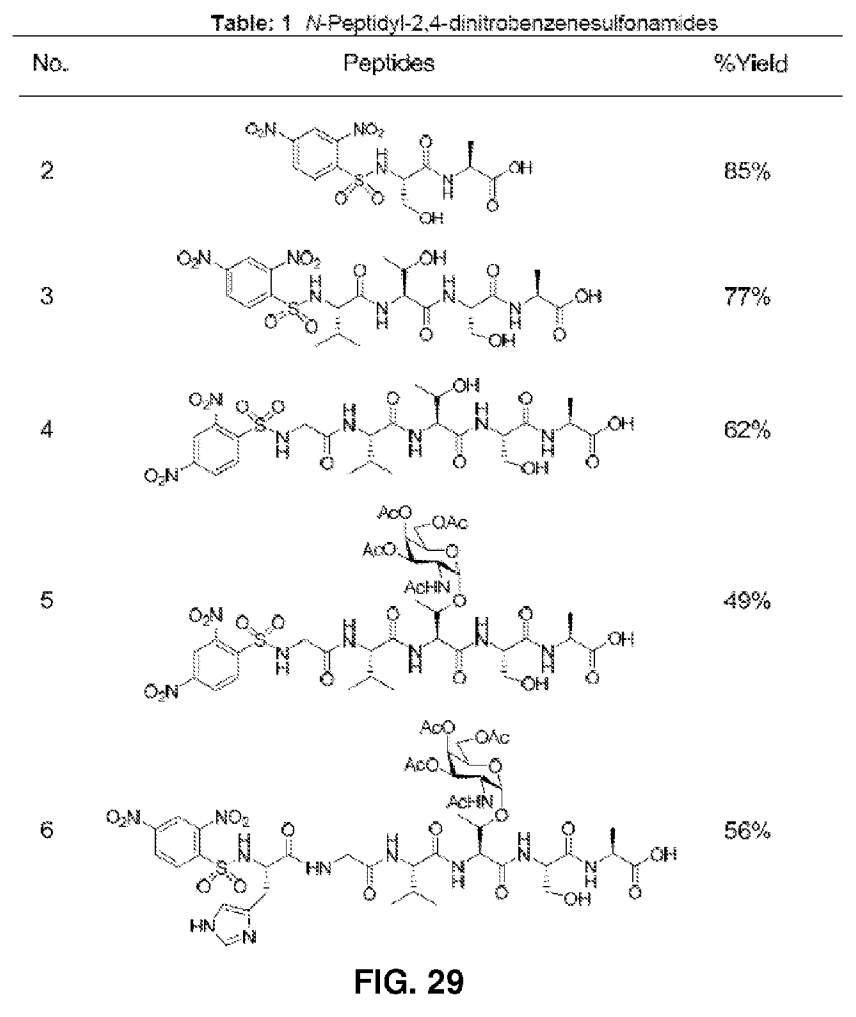

FIG. 29 is a Table 1—showing: HPLC Purified Yields of N-Peptidyl-2,4-dinitrobenzenesulfonamides.

DETAILED DESCRIPTION OF THE PREFERRED EMBODIMENTS

Figure 26:
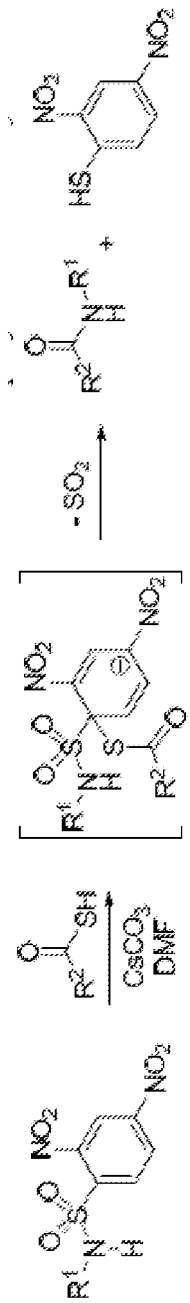
FIG. 26 is a diagram showing Scheme 1—the reaction of sulfonamides and thioacids to form amides.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Here and as follows, the term "$C_{1-n}$ alkyl" is to be understood to mean any linear or branched alkyl group containing 1 to n carbon atoms. In a non-limiting example, the term "$C_{1-6}$ alkyl" comprises groups such as methyl, ethyl, propyl, isopropyl, butyl, isobutyl, sec-butyl, tert-butyl, pentyl, isopentyl (3-methylbutyl), neopentyl (2,2-dimethylpropyl), hexyl, isohexyl (4-methylpentyl) and the like.

Accordingly, the term "$C_{1-n}$ alkoxyl" means a group composed of a $C_{1-n}$ alkyl group as defined above and an oxygen atom linked by a single covalent bond.

The term "aryl-substituted $C_{1-n}$ alkyl" is to be understood to mean a group composed of a $C_{1-n}$ alkyl group as defined above which is substituted at any position of the linear or branched carbon chain with at least one phenyl group. The phenyl group may be optionally substituted with at least one substituent selected from the group consisting of hydroxyl, $C_{1-2}$ alkoxy and halogen. Non-limiting examples of aryl-substituted $C_{1-n}$ alkyl groups include benzyl, 1-(3-hydroxylphenyl)-propane-2-yl or 1-(3-methoxyphenyl)propan-2-yl.

In its wider meaning the term "PEGylation reagent" is understood to mean a polyethylene glycol moiety or branched polyethylene moiety that has a molecular weight chosen from about 350, 550, 750, 2000 and 5000. Alternatively, the PEGylation reagents can preferably have about 2 to 400, or more polyethylene units, for example the PEGylation reagent can preferably have about 4, 7, 9, 11, 16, 20, 40, 100, 200, 400, or more units. These PEGylation reagents must be modified with a thioacid group capable of reacting with a sulfonamide moiety in the peptide to produce the PEG-peptide conjugate.

In certain preferred embodiments, the sulfonamide is a dNBS moiety.

In its narrower meaning "PEGylation reagent" is understood to mean any material such as a saccharide, polysaccharide, peptide, or polymer which has been modified with a thioacid moiety which is capable of reacting with a sulfonamide, such as the dNBS moiety, to produce an amide bond.

In one preferred embodiment, P of the compound of formula I and $R^4$ and $R^5$ of formula I is an orthogonal protecting group selected for the group consisting of Fmoc, Boc, Cbz, Npys and Alloc.

Here and as follows, "Fmoc" abbreviates fluorine-9-yl-methoxycarbonyl, "Boc" abbreviates tert-butyloxycarbonyl, "Cbz" abbreviates benzyloxycarbonyl, "Npys" abbreviates 3-nitro-2-pyridinesulfenyl and "Alloc" abbreviates allyloxycarbonyl.

Here and as follows, the term "orthogonal" related to two different protecting groups is to be understood to mean that one protecting group is removable whilst the other remains stable under the same reaction conditions.

The peptides described herein may be any peptide comprising natural or non-natural amino acids and, if chiral, in its L or D configurations or as racemate Amino acid may also be composed of side chains containing a sulfonamide moiety. Non-limiting examples of non-natural amino acids are homocysteine, homoarginine, cylcohexylalanine, ornithine, and $C^{\alpha,\alpha}$-dibenzylglycine.

The terms "side chain," and the prefix "homo" are construed in the present context in accordance with IUPAC-IUB definitions (Joint IUPAC-IUB Commission on Biochemical Nomenclature, "Nomenclature and Symbolism of Amino Acids and Peptides", *Pure Appl. Chem.* 1984, 56, 595-624).

In its wider meaning, "homo" is to be understood to mean up to nine extra methylene groups added in a linear fashion to the lysine side chain. In its narrower and preferred meaning, "homo" amounts to just one extra methylene group in the side chain.

The term "chromophoric" is construed in the present context pertain to a molecule containing a chromophore which is part of a molecule responsible for its color.

The term "fluorogenic" is construed in the present context pertain to a molecule containing a fluorophore, which is a component of a molecule which causes a molecule to be fluorescent.

In one preferred embodiment, n of the compound of formula I, III, and V, is one through fifty. In another preferred embodiment, R1 of the compounds of formula I, III, and V, are independently hydrogen, methyl, ethyl, propyl and butyl; preferably hydrogen, methyl and ethyl; and most preferably hydrogen.

In the solid-phase synthesis process that is further described herein most, or preferably all, of the functional groups in amino acid side chains are masked with permanent protecting groups that are not affected by the reaction conditions employed during the peptide chain assembly of such synthesis process.

The α-amino group of each amino acid to be coupled is temporarily protected with a protecting group that is preferably orthogonal to the side chain protecting groups, except for the last amino acid to couple, which, optionally, can be removed using the same deblocking chemistry as the side chain protecting groups. After anchoring of the first amino acid, as described herein, the temporary a-amino protecting group is removed.

All suitable protecting groups known in the art may be used for both protecting the side chain functions and the α-amino group of the amino acids or peptides used in steps (b) and (c) as set forth herein.

Non-limiting examples of suitable protecting groups include: fluoren-9-ylmethoxycarbonyl (Fmoc), benzyloxycarbonyl (Cbz), tert-butyloxycarbonyl (Boc), 2-(4-biphenylyl)-isopropyloxycarbonyl (Bpoc), acetamidomethyl (Acm), acetyl (Ac), allyl (All), allyloxycarbonyl (Alloc), benzoyl (Bz), benzyl (Bzl), 3-carboxypropanoyl (Sue), 5-sulfonyl-2,2,4,6,7-pentamethylbenzofuran (Pbf) and trityl (Trt).

In one embodiment, P of the compound of formula I, an $R^4$ of formula III, and $R^5$ of formula V is Fmoc and the N-terminally protected amino acids or peptides of steps (b) and (c) in method I are Fmoc-protected, except for the N-terminally protected amino acid or peptide of the lastly repeated step (e) or (f) of method II, which is optionally protected by an protecting group being orthogonal to Fmoc, preferably being Boc.

Coupling reagents, coupling additives and aprotic, polar solvents such as, for example, dimethylformamide or N-methylpyrrolidone, or mixtures thereof, are well known in the art and are described e.g. in Bodanszky, "Principles of Peptide Synthesis," $2^{nd}$ ed., Springer Verlag, 1993).

Non-limiting examples of suitable coupling reagents are diisopropylcarbodiimide (DIC), 1,3-dicyclohexylcarbodiimide (DCC), N-ethyl-N'-(3-dimethylaminopropyl)-carbodiimide (EDC), benzotriazol-1-yl-oxy-tripyrrolidinophosphonium hexafluorophosphate (PyBOB), O(1H-benzotriazol-1-yl)-N,N,N',N'-tetramethyluronium tetrafluoroborate (HBTU) and O-(1H-6-chlorobenzotriazol-1-yl)-N,N,N',N'-tetramethyluronium tetrafluoroborate (TCTU). Examples for coupling additives are N-hydroxybenzotriazole (HOBt), 6-chloro-N-hydroxybenzotriazole (6-chloro-HOBt), N-hydroxysuccinimide and N-hydroxy-3,4-dihydro-4-oxo-1,2,3-benzotriazine (HOOBt).

In certain embodiments, the amount of each amino acid or peptide used in steps (b) and (c) of method 1 is between 1 and 3 equivalents.

The solid-phase support may be a suitable solid-phase resin, such as an activated halogen, an activated derivative of hydroxy or carboxy functionalized resin or grafted linker-resin composite. The polymer matrix of the resin may be, for example, polystyrene, polyethyleneglycol (PEG), cross-linked PEG, polyamide, polyvinylalcohol (PVA) or polyoxyalkylene. The support may be a pure or a mixed resin, including block-copolymers or grafted resins such as PVA grafted on PEG resin, PEG-grafted polystyrene-divinylbenzene (PS-DVB) resins, polyoxyethylene resins grafted onto an inner polystyrene matrix, wherein the functionalized groups for coupling being exposed on the polyoxyethylene branches.

Non-limiting examples are 2-chlorotrityl chloride polystyrene (2-CTC) resin, bromo-(4-methyl-phenyl)-methyl polystyrene resin, bromo-(4-methoxyphenyl)-methyl polystyrene resin, Merrifield resin or Wang resin.

The term "fluorous tag" is to be understood to mean any $C_{1-n}$ alkyl" or aryl-substituted $C_{1-n}$ alkyl as defined above in which the hydrogen atoms of the moiety have been replaced by one or more fluorine atoms.

Non-limiting examples of fluorous tag reagents for peptide synthesis include 4-(1H,1H,2H,2H-Perfluorodecyl-1-thio) phenol and 4-[3-(perfluorooctyl)propyl-1-oxy]benzyl alcohol.

Referring now to the FIGURES, the inventors herein have now discovered a method for synthesizing difficult and/or long peptide and peptide conjugates. Until the present inventors' discovery, the reaction of sulfonamides and thioacids to form amines (as generally shown in the Scheme 1 in the PRIOR ART—FIG. 26), has not been used to form polypeptides.

FIG. 26 shows that the use of the dNBS group as an N-sulfonamide derivative 1 facilitates the formation of amides 3 in the presence of thioacids (Messeri, et al. *Tetrahedron Lett.* 1998, 39, 1669-72; Messeri, et al. *Tetrahedron Lett.* 1998, 39, 1673-6). The mechanism involves the attack of the thioacid on the sulfonamide to form a Meisenheimer complex 2. The nitrogen of the sulfonamide ultimately attacks the adjacent thioester with extrusion of $SO_2$. This chemistry was also shown to be amenable to the coupling of hindered amino acid derivatives to form native dipeptides and a tetrapeptide using dNDBS modified single amino acids or dNBS dipeptides using exclusively solution phase methods (Crich, et al. *Org. Lett.* 2007, 9, 4423-4426, Crich, et al. *Org. Lett.* 2007, 9, 5323-5325). Further demonstrating the scope of the dNBS-thioacid chemistry, β-N-dNBS-glycosylsulfonamides have been shown to provide β-configured glycosyl amino acids common to most N-linked glycopeptides/proteins when reacted with amino thioacids (Talan et al. *Carbohydr. Res.* 2009, 344, 2048-2050).

The reaction between dNBS-modified amines and thioacids can be performed at room temperature and is complete in thirty minutes to two hours. The observed yields of this ligation are comparable with other methods such as the Staudinger ligation reaction (Doores et al. *Chem. Comm.* 2006, 1401-1403; He et al. *Org. Lett.* 2004, 6, 4479-4482. Györgydeák, et al. *Bioorg. Med. Chem.* 2004, 12, 4861-4870).

Aside from the chemistry underlying a given amide bond forming reaction, its adoption depends on the straightforward synthesis of the requisite fragments to be coupled. Some N-peptidyl arylsulfonamides have been reported to be amenable to SPPS synthesis. For example, ortho-nitrobenzenesulfonamides (o-NBS) and para-nitrobenzenesulfonamides (p-NBS) have been coupled to the N-terminus of a peptide bound to Rink amide 4-methylbenzhydrylamine (MBHA) resin (Miller, et al. *J. Am. Chem. Soc.* 1997, 119, 2301-2302) while o-NBS-amino acids have been synthesized off-resin and used in SPPS (Miller, et al. *J. Am. Chem. Soc.* 1998, 120, 2690-2691). However, in both instances, the N-arylsufonyl group was used as protecting group to aid in the controlled alkylation of the N-terminus, and was removed afterwards.

The inventors herein have now improved upon the methods for synthesizing difficult and/or long peptide and peptide conjugates.

Methods

Figure 27:
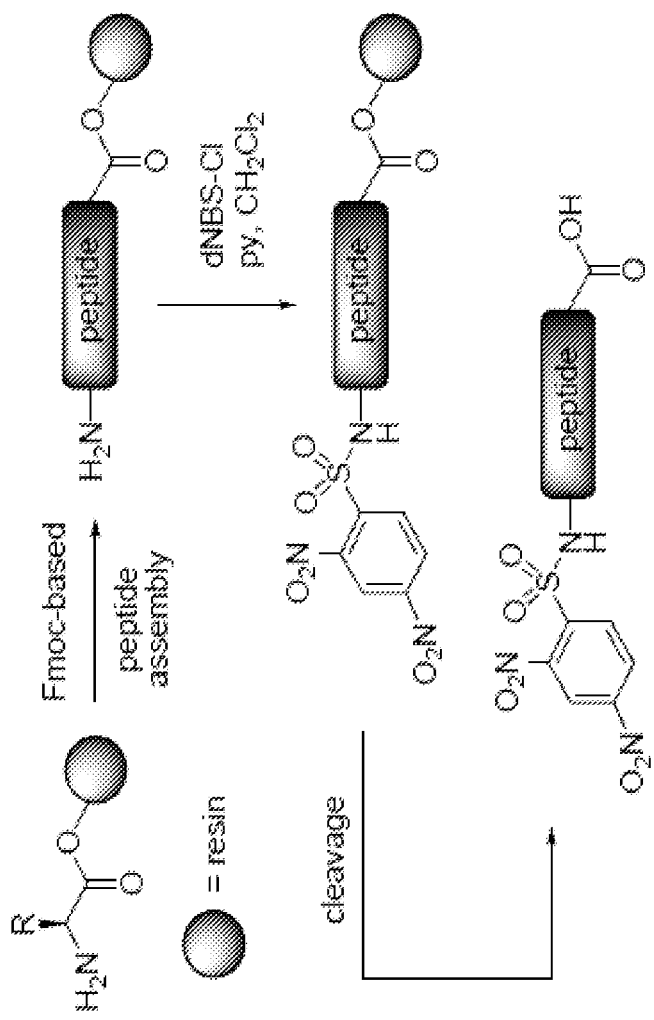
FIG. 27 is a diagram showing Scheme 2 of a method for the synthesis of N-peptidylsulfonamides.
Figure 28:
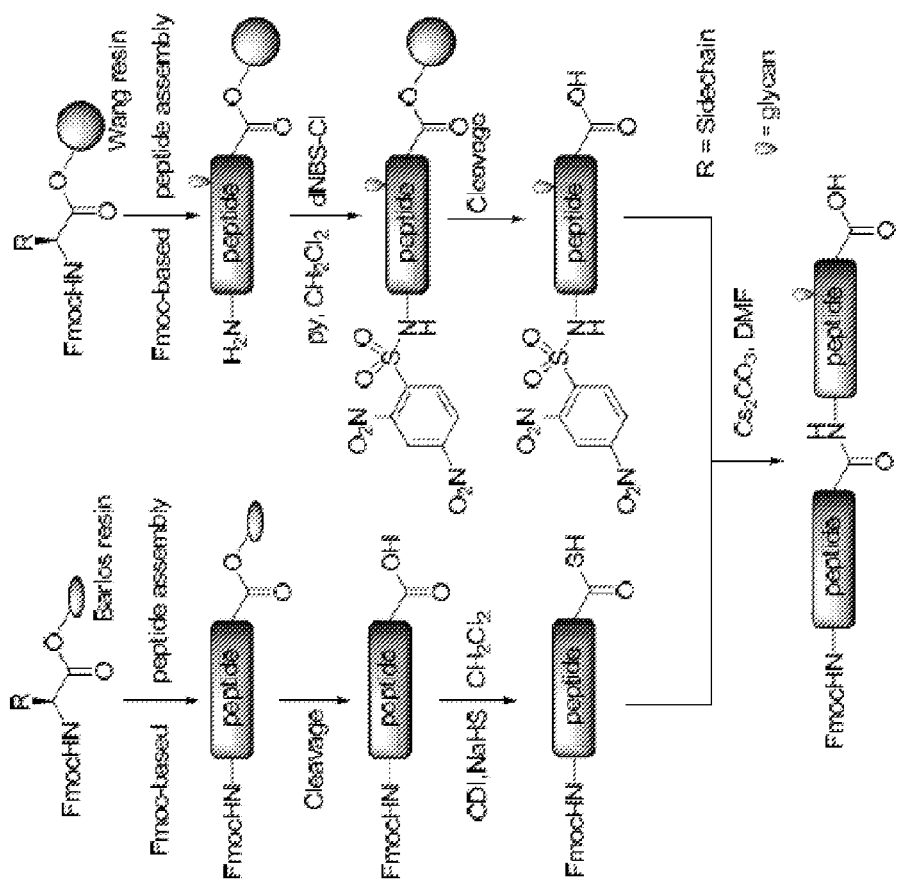
FIG. 28 is a diagram showing Scheme 3 of a method for mixed phase synthesis of peptide sequences.

Referring first to FIG. 27 FIG. 28, there are shown general schema of the methods described herein.

FIG. 27 shows Scheme 2 where the method that allows the installation of a sulfonamide group (such as, but not limited to a dNBS group) directly to the N-terminus of a growing peptide on a resin or a fluorous tag without the need to synthesize other sulfonamide-modified amino acids or peptides.

FIG. 28 shows a general strategy for mixed phase synthesis of peptide sequences.

Figure 30:
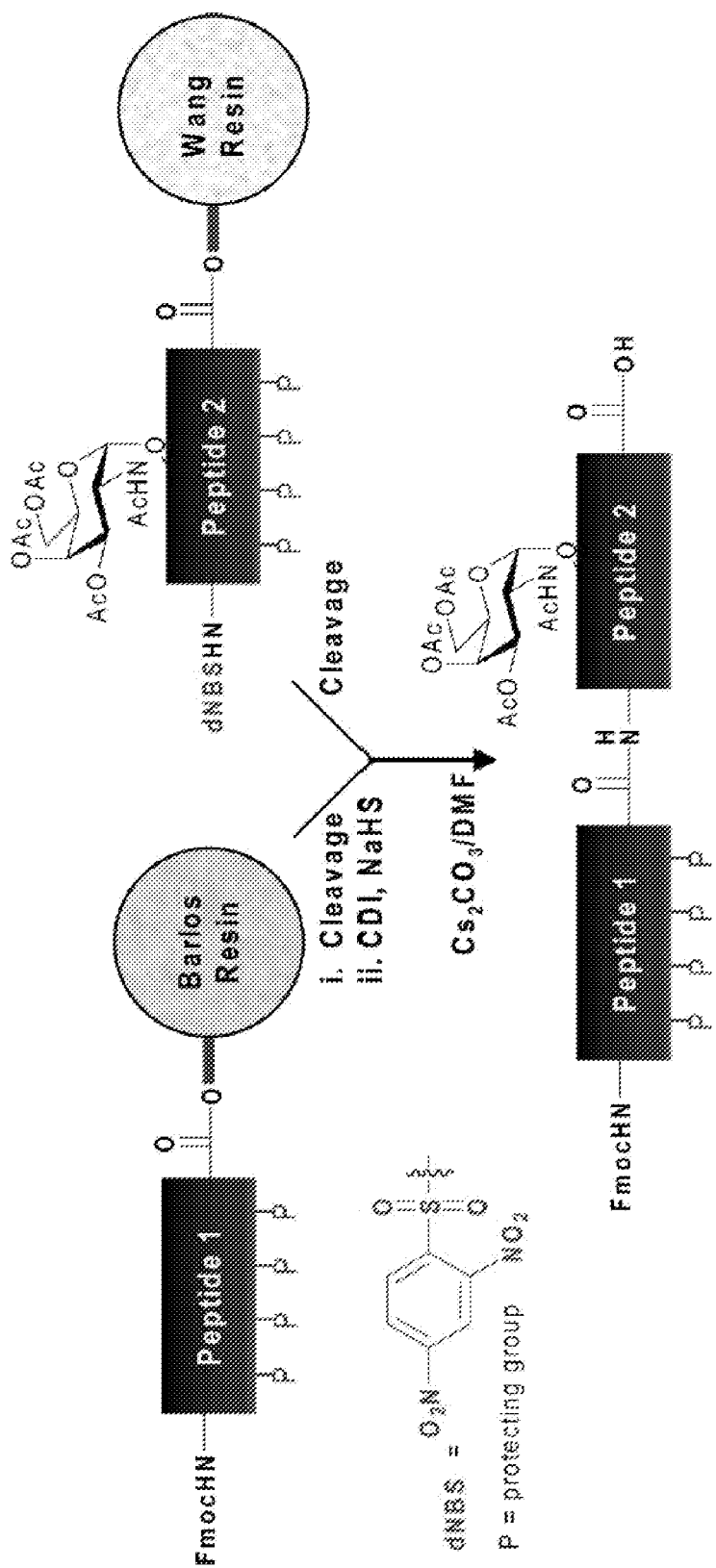
FIG. 30 is a diagram showing Scheme 3 of another method for mixed phase synthesis of peptide sequences.

FIG. 30 shows a general strategy for mixed phase synthesis of peptide sequences, including the solid phase peptide synthesis (SPPS) and coupling of N-peptidyl and N-glycopeptidyl 2,4-dinitrobenzenesulfonamides (dNBS) with C-terminal peptidyl thioacids. The resulting N-dDNBS peptides were coupled to generate longer peptides. Ligation reactions were complete within 15 to 20 minutes.

The methods described herein also allow for the sulfonamide group to be attached site specifically to any position on an amino acid side chain during a solid-phase peptide synthesis (SPPS) process.

In certain embodiments, the sulfonamide group can remain intact through a cleavage step of the peptide from the resin in order to affect the desired amide bond formation reaction with a thioacid off-resin, as is required in the case of mixed methods for peptide of peptide conjugate synthesis.

In certain embodiments, the methods are useful for off-resin peptide formation and/or conjugation reactions.

In other embodiments, the method is useful for preparing dNBS- or other sulfonamide-modified peptides that can then be coupled with thioacids while the dNBS- or other sulfonamide-modified peptides remain attach to a resin or a fluorous tag.

In another broad aspect, there is provided herein compounds derived from one or more of the methods described herein.

Method 1

One embodiment of a method for synthesizing sulfonamide-modified peptides and peptide conjugates starting from a compound I, is shown:

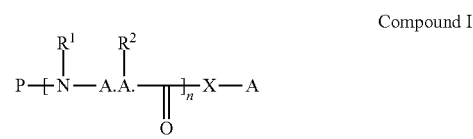

Compound I wherein A is a solid-phase or fluorous support or a linker grafted to a solid-phase or fluorous support;

X is O, NH or $NR^1$, wherein $R^1$ is independently hydrogen, $C_{1-n}$ alkyl, or $C_{1-n}$ alkoxyl, or aryl-substituted $C_{1-n}$ alkyl;

A.A. is an optimally protected amino acid or optimally protected peptide;

$R^2$ represents any optimally protected natural or unnatural amino acid side chain.

In certain embodiments, the side chain can also contain a sulfonamide moiety such as, but not limited to:

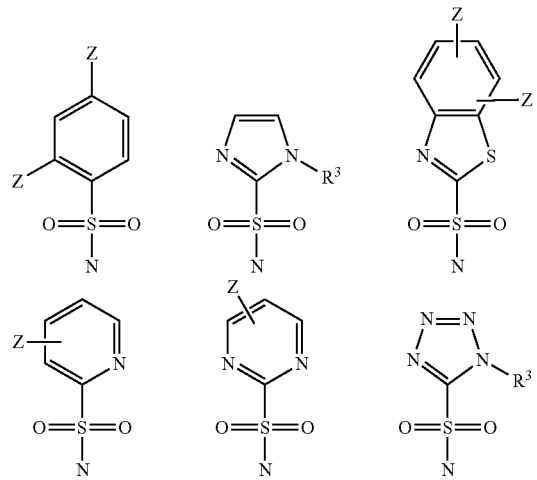

wherein, Z is independently $NO_2$, $CF_3$, —COR, F;

wherein R is $NH_2$ or $C_1$, alkyl, or other electron withdrawing group;

$R^3$ is $C_{1-n}$ alkyl, or aryl-substituted $C_{1-n}$ alkyl, and N is part of a primary or secondary sulfonamide; and, wherein, n is a positive integer; and P is an amine protecting group orthogonal to the bond between X and A.

In an embodiment of the invention, P of the compound of formula I, and $R^4$ of formula III, and $R^5$ of formula V is an orthogonal protecting group selected from the group consisting of Fmoc, Boc, Cbz, Npys and Alloc.

After a desired number of amino acids are assembled together by de-protecting each amino acid's N-terminus, until the desired peptide is formed. After the desired peptide is formed, the N-terminus is deprotected for a final time such that a sulfonamide group is attached to the N-terminus In certain embodiments, the sulfonamide group can be formula II, such as, but not limited to:

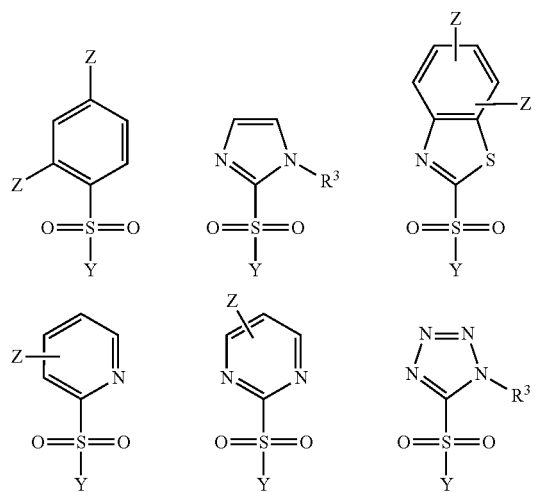

wherein, Z is independently NO$_2$, CF$_3$, —COR, F;

wherein R is NH$_2$ or C$_{1-n}$ alkyl, or other electron withdrawing group;

R$^3$ is C$_{1-n}$ alkyl, or aryl-substituted C$_{1-n}$ alkyl; and,

Y is a halogen, azido group, OH, or sulfonyl activating group.

The Method generally includes the steps of:

a) deprotecting the N-terminal amino function of a first amino acid;

b) coupling an N-terminally protected amino acid (or a peptide having a free or activated carboxylic acid function) with the deprotected N-terminal amino acid function of step (a), thus elongating the compound of formula I, c) optionally, repeating at least once steps (a) and (b), wherein the N-terminally protected amino acid or peptide is identical or different to that of the preceding step (b), d) optionally, repeating step (a), e) optionally, coupling a sulfonyl group of formula II with the deprotected amino acid function of step (d), thus creating a compound III, Compound III

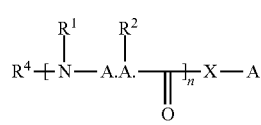

wherein A is a solid-phase or fluorous support or a linker grafted to a solid-phase or fluorous support;

X is O, NH or Me,

R$^1$ is independently hydrogen, C$_{1-10}$ alkyl, or C$_{1-n}$ alkoxyl, or aryl-substituted C$_{1-n}$ alkyl;

A.A. is an optimally protected amino acid or optimally protected peptide;

R$^2$ is an optimally protected natural or unnatural amino acid side chain.

The side chain can also contain the sulfonamide moiety selected from the following list,

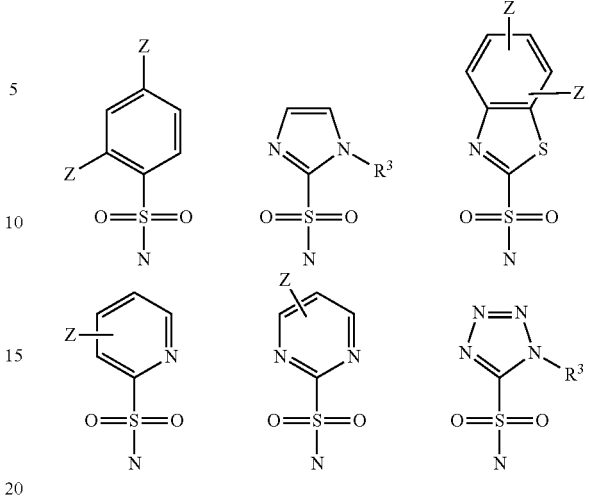

wherein Z is independently NO$_2$, CF$_3$, —COR, F;

R is NH$_2$ or C$_{1-n}$ alkyl, or other electron withdrawing group,

R$^3$ is C$_{1-n}$ alkyl, or aryl-substituted C$_{1-n}$ alkyl, and

N is part of a primary or secondary sulfonamide;

wherein, R$^4$ represents an amine protecting group orthogonal to the bond between X and A, or a moiety.

For example, R$^4$ can comprises:

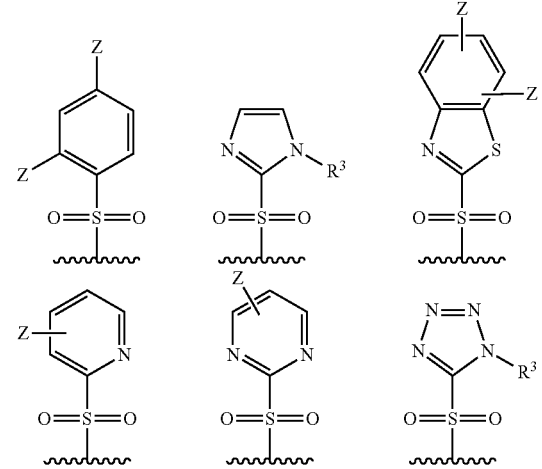

wherein Z is independently NO$_2$, CF$_3$, —COR, F;

wherein R is NH$_2$ or C$_{1-n}$ alkyl, or other electron withdrawing group,

R$^3$ is C$_{1-n}$ alkyl, or aryl-substituted C$_{1-n}$ alkyl, wherein, n is a positive integer;

In certain embodiments, the method further comprises the steps of:

(f) optionally, cleaving the resulting peptide from A, (g) optionally removing all the protecting groups that remain after step (f), (h) isolating and optionally purifying the peptide thus obtained, (i) reacting the compound III with a compound IV; and (j) isolating and optionally purifying the peptide or peptide conjugate thus obtained.

In the method described above A is a solid-phase or fluorous support or a linker grafted to a solid-phase or fluorous support or hydrogen;

X is O, OH, NH, $NH_2$ or $NR^1$, $NHR^1$, wherein $R^1$ is independently a hydrogen, $C_{1-n}$ alkyl, $C_{1-n}$ alkoxyl, aryl-substituted $C_{1-n}$ alkyl;

A.A. is an optimally protected amino acid or optimally protected peptide;

A.A. is an unprotected amino acid or unprotected peptide;

n is a positive integer;

$R^2$ represents any optimally protected or unprotected natural or unnatural amino acid side chain.

In certain embodiments, the side chain can also contain the sulfonamide moiety as follows:

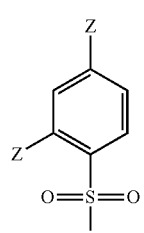 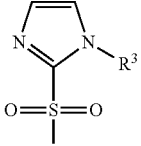 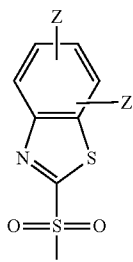

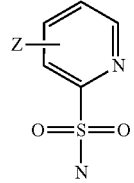 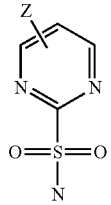 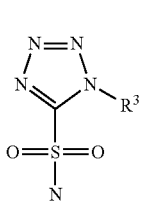

wherein, Z is independently $NO_2$, $CF_3$, —COR, F;

R is $NH_2$ or $C_1$, alkyl, or other electron withdrawing group, $R^3$ is $C_{1-n}$ alkyl, or aryl-substituted $C_{1-n}$ alkyl, and N is part of a primary or secondary sulfonamide;

and wherein, $R^4$ represents an amine protecting group orthogonal to the bond between X and A, hydrogen, or moiety selected from the following list,

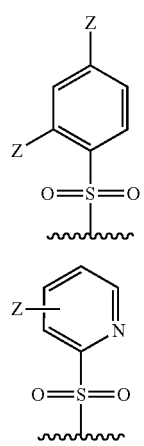 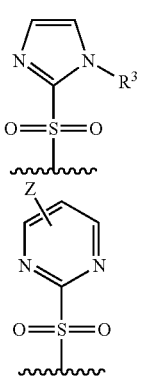 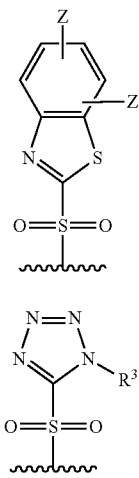

wherein, Z is independently $NO_2$, $CF_3$, —COR, F wherein R is $NH_2$ or $C_1$, alkyl, or other electron withdrawing group, $R^3$ is $C_{1-n}$ alkyl, or aryl-substituted $C_{1-n}$ alkyl.

The compound IV has the formula:

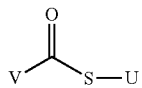

Compound IV wherein U is hydrogen or cation; and,

V is an optimally protected amino acid, optimally protected peptide, unprotected amino acid, unprotected peptide, saccharide moiety, polysaccharide moiety, polymer, polyethylene glycol moiety, branched polyethylene moiety, chromophoric or fluorogenic moiety, or any chemical entity known in the art of organic chemistry to form a compound V of the formula,

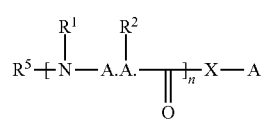

Compound V

In compound V,

A is a solid-phase or fluorous support or a linker grafted to a solid-phase or fluorous support or hydrogen;

X is O, OH, NH, $NH_2$ or $NR^1$, $NHR^1$;

wherein $R^1$ is independently a hydrogen, $C_{1-n}$ alkyl, $C_{1-n}$ alkoxyl, aryl-substituted $C_{1-n}$ alkyl;

A.A. is an optimally protected amino acid or optimally protected peptide;

A.A. is an unprotected amino acid or unprotected peptide;

n is a positive integer;

$R^2$ represents any optimally protected or unprotected natural or unnatural amino acid side chain, if the $R^2$ side chain previously contained a sulfonamide form the list above the sulfonamide is now transformed to an amide with the structure,

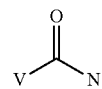

wherein V is an optimally protected amino acid, optimally protected peptide, unprotected amino acid, unprotected peptide, saccharide moiety, polysaccharide moiety, polymer, polyethylene glycol moiety, branched polyethylene moiety, chromophoric or fluorogenic moiety, or any chemical entity known in the art of organic chemistry, and N is part of a primary or secondary amide;

$R^5$ represents an amine protecting group orthogonal to the bond between X and A, H, or if $R^5$ previously contained a sulfonyl group from the list above the sulfonyl is now transformed to an acyl group with the structure,

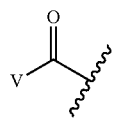

wherein V is an optimally protected amino acid, optimally protected peptide, unprotected amino acid, unprotected peptide, saccharide moiety, polysaccharide moiety, polymer, polyethylene glycol moiety, branched polyethylene moiety, chromophoric or fluorogenic moiety, or any chemical entity known in the art of organic chemistry.

Compounds

In another broad aspect, there are provided herein compounds III having the general formula:

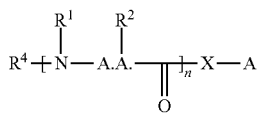

III wherein A is a solid-phase or fluorous support or a linker grafted to a solid-phase or fluorous support or hydrogen;

X is O, OH, NH, $NH_2$ or $NR^1$, $NHR^1$, wherein $R^1$ is independently a hydrogen, $C_{1-n}$ alkyl, $C_{1-n}$ alkoxyl, aryl-substituted $C_{1-n}$ alkyl;

A.A. is an optimally protected amino acid or optimally protected peptide;

A.A. is an unprotected amino acid or unprotected peptide;

n is a positive integer;

$R^2$ represents any optimally protected or unprotected natural or unnatural amino acid side chain, where the side chain can also contain the sulfonamide moiety such as:

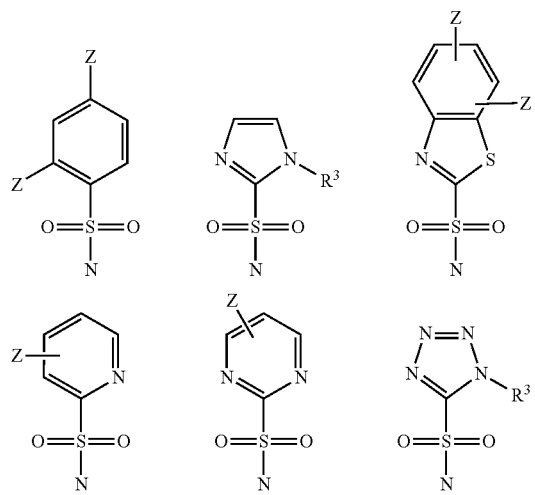

wherein Z is independently $NO_2$, $CF_3$, —COR, F; wherein R is $NH_2$ or $C_{1-n}$ alkyl, or other electron withdrawing group, $R^3$ is $C_{1-n}$ alkyl, or aryl-substituted $C_{1-n}$ alkyl, and N is part of a primary or secondary sulfonamide;

wherein, $R^4$ represents an amine protecting group orthogonal to the bond between X and A, hydrogen, or moiety such as:

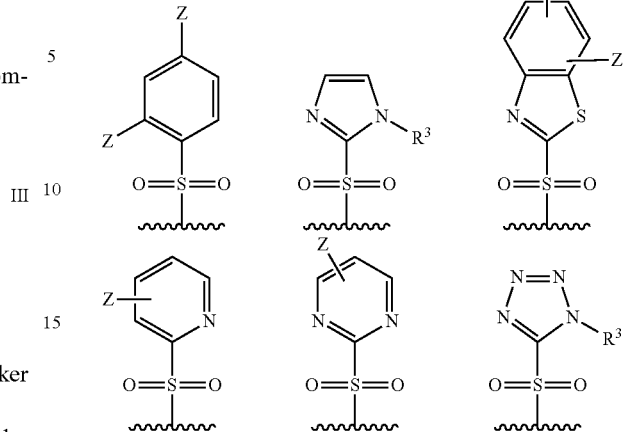

wherein Z is independently $NO_2$, $CF_3$, —COR, F wherein R is $NH_2$ or $C_{1-n}$ alkyl, or other electron withdrawing group, $R^3$ is $C_{1-n}$ alkyl, or aryl-substituted $C_{1-n}$ alkyl.

In certain embodiments, the compound III has at least three amino acid units and contains at least one sulfonamide group selected from the list of sulfonamides.

In certain preferred embodiments, the compound III includes compounds where n is an integer between one and fifty. In an embodiment of the invention, $R^1$ of the compounds of formula I, III, and V, are independently hydrogen, methyl, ethyl, propyl and butyl; preferably hydrogen, methyl and ethyl; and most preferably hydrogen.

In another embodiment of the invention, A of the compound III is H. Another embodiment is the compound III, wherein A.A. is an unprotected amino acid or unprotected peptide. Another embodiment is the compound of formula III, wherein Z is $NO_2$.

EXAMPLES

The following experiments are meant to illustrate this invention but are not intended to limit in any way.

Materials.

Fmoc Ala-preloaded Wang resin (substitution: 0.6 mmol/g) was procured from Novabiochem Amino acids and HOBt were purchased from Chem-Impex International and PyBOP was acquired from Acros Organics. Fmoc-Ac₃-Tn-α-Thr-OH was obtained from Sussex Research. All other fine chemicals were sourced from the following commercial suppliers: Acros Organics, Alfa Aesar, Fisher Scientific and Sigma-Aldrich. Pyridine, and peptide grade DMF and DIEA were dried over 3 Å and 4 Å molecular sieves, respectively. Anhydrous $CH_2Cl_2$ was freshly distilled over $CaH_2$. Extra dry MeOH was used as received.

General Procedures.

RP-HPLC analyses were carried out on a Shimadzu LC-20AT prominence liquid chromatograph equipped with DGU-20A₃ prominence degasser. Data was processed with Shimadzu LC solution software. Analytical RP-HPLC was performed on a Premier C8 column (150×4.6 mm, 5 μm) with a flow rate of 1.0 mL/min, whereas semi-preparative RP-HPLC was accomplished on a Restek UltraC8 column (150×10.0 mm, 5 μm) with a flow rate of 5.0 mL/min Samples were eluted with a gradient of water (0.1% TFA) and MeOH (0.1% TFA) over a period of 35 min and UV detection at 254 nm. Proton and carbon nuclear magnetic resonance spectra (¹H NMR and $^{13}$C NMR) were recorded on either INOVA-600 ($^1$H NMR 600 MHz; $^{13}$C NMR 150 MHz) or Varian VXR-400 ($^1$H NMR 400 MHz; $^{13}$C NMR 100 MHz) spectrometers with solvent resonance as internal standard (MeOH-d$_4$: $^1$H NMR at δ 3.31, $^{13}$C NMR at δ 49.15; CD$_3$CN: $^1$H NMR at δ 1.94). The $^1$H NMR data are presented as follows: chemical shift, multiplicity (s=singlet, d=doublet, dd=doublet of doublet, t=triplet, q=quartet, m=multiplet), coupling constants in Hertz, integration, and assignments. $^1$H-$^1$H gCOSY was performed on the INOVA-600 spectrometer. Low resolution mass spectra were taken on Esquire-LC electrospray ionization (ESI) mass spectrometer operated in the positive ion mode.

Solid-Phase Peptide Synthesis.

Peptides were manually assembled on Fmoc Ala-preloaded Wang resin (150 mg) using Fmoc/tBu strategy. The reactions were performed in a 20 mL syringe reactor cartridge with agitation provided by a stream of N$_2$. The following amino acids were used: Fmoc-Ser(OtBu)-OH, Fmoc-Thr(OtBu)-OH, Fmoc-Val-OH, Fmoc-Gly-OH and Fmoc-Ac$_3$-Tn-α-Thr-OH.

The synthesis involved the following steps:

(i) Fmoc deprotection with 20 or 40% piperidine in DMF (3 mL) for 25 min;

(ii) Kaiser test;

(iii) washing with DMF (3×3 mL, 5 min/wash);

(iv) coupling of Fmoc amino acid (2 eq) for 1-2 h with pre-activation (2 min) in PyBOP (2 eq), HOBt (2 eq), DIEA (4 eq) and DMF;

(v) Kaiser test;

(vi) washing with DMF (3×3 mL, 5 min/wash).

Double or triple deprotection and couplings were performed as indicated by the Kaiser test. Coupling involving Fmoc-Ac$_3$-Tn-α-Thr-OH was carried out for 7 h using the same amount of reagents as mentioned above. After assembly, the Fmoc group was removed, the resin washed with DMF (3×3 mL, 5 minutes/wash), followed by CH$_2$Cl$_2$ (3×3 mL, 5 minutes/wash). The resin was transferred to a 20 mL scintillation vial for reaction with 2,4-dinitrobenzenesulfonyl chloride as described below. The peptide was released from the resin following treatment with TFA/H$_2$O (95:5), unless otherwise noted, for 4 h under N$_2$ atmosphere. The mixture was filtered, washed with the cleavage cocktail (1-2 mL), then with a liberal amount of CH$_2$Cl$_2$, unless otherwise stated. The filtrate was concentrated to dryness in vacuo and the crude peptide was purified. Yields are based on the resin loading provided by the manufacturer.

General Procedure for N-Terminal Sulfonation (Method A).

To the pre-swollen peptidyl resin was added 2,4-dinitrobenzenesulfonyl chloride (0.096 g, 0.36 mmol), CH$_2$Cl$_2$ (1.0 mL) and pyridine (0.12 mL, 1.44 mmol). The mixture was stirred slowly (to prevent resin attrition) at room temperature under N$_2$ atmosphere. After 4 h, the mixture was washed with CH$_2$Cl$_2$ (1×6 mL, 5 min/wash), DMF (3×3 mL, 5 min/wash) and CH$_2$Cl$_2$ (3×3 mL, 5 min/wash). The above coupling procedure was performed twice. Kaiser test was used to monitor the completion of the reaction. The resin was given a final MeOH wash (3×3 mL, 5 min/wash) prior to drying in high vacuum.

Improved General Procedure for N-Terminal Sulfonation (Method B).

To the pre-swollen peptidyl resin was added 2,4-dinitrobenzenesulfonyl chloride (0.096 g, 0.36 mmol), CH$_2$Cl$_2$ (1.0 mL) and pyridine (0.12 mL, 1.44 mmol). The mixture was stirred slowly (to prevent resin attrition) at room temperature under N$_2$ atmosphere for 3 h. Afterwards, 2,4-dinitrobenzenesulfonyl chloride (0.096 g, 0.36 mmol) and pyridine (0.24 mL, 2.88 mmol) were added to the mixture and stirring was continued for 3-3.5 h more. The mixture was washed with CH$_2$Cl$_2$ (1×6 mL, 5 min/wash), DMF (3×3 mL, 5 min/wash), CH$_2$Cl$_2$ (3×3 mL, 5 min/wash) and finally MeOH (3×3 mL, 5 min/wash) and the resin was dried in high vacuum. Kaiser test was used to monitor the completion of the reaction.

Example 1

Solid Phase Synthesis of dNBS-Alanine (1)

After N-terminal capping following the general procedure (Method A) described earlier, the sulfonamide was cleaved from the resin (140 mg) upon treatment with the cleavage cocktail (1.4 mL).

The crude sulfonamide was purified by flash column chromatography on silica gel ((230-400 mesh, 6×1.3 cm) using MeOH/CH$_2$Cl$_2$/CH$_3$COOH (5:95:0.6) to give a yellow solid (11.6 mg, 40%). $^1$H NMR (600 MHz, MeOH-d$_4$) δ 8.72 (d, J=2.4 Hz, 1H), 8.59 (dd, J=2.4, 8.4 Hz, 1H), 8.34 (d, J=8.4 Hz, 1H), 4.19 (q, J=7.2 Hz, 1H), 1.45 (d, J=7.2 Hz, 3H); $^{13}$C NMR (400 MHz, MeOH-d$_4$) δ 174.92, 151.42, 149.41, 140.77, 133.51, 127.92, 121.37, 53.58, 19.53; ESI-MS calcd for C$_9$H$_9$N$_3$NaO$_8$S [M+Na]$^+$ 342.00. found 342.0.

Example 2

Solid Phase Synthesis of dNBS-Ser-Ala-OH (2)

After N-terminal capping following the general procedure (Method A) described earlier, a portion (18.4 mg) of the recovered resin (147 mg) was treated with the cleavage cocktail (0.2 mL) to afford the crude peptide.

The crude peptide was purified by reverse-phase flash column chromatography on a PrepSep C18 plug (2×1.5 cm) using 60 mL each of the following solvents in the order indicated: MeOH/H$_2$O (1:3), MeOH/H$_2$O (1:1), MeOH/H$_2$O (3:1) and MeOH to afford a white solid (3.9 mg, 85%). $^1$H NMR (600 MHz, MeOH-d$_4$) δ 8.75 (d, J=2.4 Hz, 1H), 8.59 (dd, J=2.4, 9.0 Hz, 1H), 8.35 (d, J=8.4 Hz, 1H), 4.16 (t, J=6.0 Hz, 1H, Ser-β-CH), 4.13 (q, J=7.2 Hz, 1H, Ala-α-CH), 3.81-3.75 (m, 2H, Ser-α-CH, and Ser-β-CH), 1.28 (d, J=7.2 Hz, 3H, Ala-CH$_3$); ESI-MS calcd for C$_{12}$H$_{14}$N$_4$NaO$_{10}$S [M+Na]$^+$ 429.03. found 429.2.

Example 3

Solid Phase Synthesis of dNBS-Val-Thr-Ser-Ala-OH (3) (SEQ ID NO: 1)

After N-terminal capping following the improved general procedure (Method B) described earlier, a portion (20.4 mg) of the recovered resin (158 mg) was treated with the cleavage cocktail (0.2 mL) to give the crude peptide.

The crude peptide was purified by semi-preparative RP-HPLC and freeze-dried to afford a white fluffy hygroscopic solid (5.4 mg, 77%). $^1$H NMR (600 MHz, MeOH-d$_4$) δ 8.74 (d, J=2.4 Hz, 1H), 8.59 (dd, J=2.4, 9.0 Hz, 1H), 8.35 (d, J=9.0, 1H), 4.40 (t, J=5.4 Hz, 1H, Ser-α-CH), 4.38-4.32 (m, 1H, Ala-α-CH), 4.17 (d, J=4.2 Hz, 1H, Thr-α-CH), 3.97 (d, J=6.6 Hz, 1H, Val-α-CH), 3.94-3.93 (m, 1H, Thr-β-CH), 3.81 (dd, J=6.0, 11.4 Hz, 1H, Ser-β-CH), 3.74 (dd, J=4.8, 11.4 Hz, 1H, Ser-β-CH), 2.11 (sextet, J=6.6 Hz, 1H, Val-β-CH), 1.39 (d, J=7.2 Hz, 3H, Ala-CH$_3$), 1.00 (d, J=6.0 Hz, 3H, Thr-CH$_3$), 0.99 (d, J=6.6 Hz, 3H, Val-CH$_3$), 0.93 (d, J=7.2 Hz, 3H, Val-CH$_3$); ESI-MS calcd for C$_{21}$H$_{30}$N$_6$NaO$_{13}$S [M+Na]$^+$ 629.15. found 629.3.

Example 4

Solid Phase Synthesis of
dNBS-Gly-Val-Thr-Ser-Ala-OH (4) (SEQ ID NO: 2)

After N-terminal capping following the improved general procedure (Method B) described earlier, a portion (20.3 mg) of the recovered resin (170 mg) was treated with the cleavage cocktail (0.2 mL) to give the crude peptide.

The crude peptide was purified by semi-preparative RP-HPLC and freeze-dried to afford a white fluffy solid (4.5 mg, 62%). $^1$H NMR (600 MHz, CD$_3$CN) ∈ 8.65 (d, J=2.4 Hz, 1H), 8.51 (dd, J=2.4, 8.4 Hz, 1H), 8.26 (d, J=8.4 Hz, 1H), 7.26 (d, J=6.6 Hz, 1H, NH), 7.21-7.14 (m, 3H, Val-NH, Thr-NH, and Ser-OH), 4.34-4.28 (m, 2H, Ser-α-CH, and Ala-α-CH), 4.26 (dd, J=3.0, 7.2 Hz, 1H, Thr-α-CH), 4.18-4.14 (m, 1H, Thr-β-CH), 4.05 (t, J=7.2 Hz, 1H, Val-α-CH), 3.96 (d, J=17.4 Hz, 1H, Gly-α-CH), 3.92 (d, J=17.4 Hz, 1H, Gly-α-CH), 3.80 (dd, J=4.2, 12.0 Hz, 1H, Ser-β-CH), 3.67 (dd, J=4.2, 11.4 Hz, 1H, Ser-β-CH), 2.09-2.04 (m, 1H, Val-β-CH), 1.34 (d, J=7.2 Hz, 3H, Ala-CH$_3$), 1.09 (d, J=6.6 Hz, 3H, Thr-CH$_3$), 0.88 (d, J=3.6 Hz, 3H, Val-CH$_3$), 0.87 (d, J=3.6 Hz, 3H, Val-CH$_3$); ESI-MS calcd for C$_{23}$H$_{33}$N$_7$NaO$_{14}$S [M+Na]$^+$ 686.17. found 686.3.

Example 5

Solid Phase Synthesis of dNBS-Gly-Val-(Ac$_3$-Tn-α-Thr)-Ser-Ala-OH (5) (SEQ ID NO: 3)

After N-terminal capping following the improved general procedure (Method B) described earlier, a portion (20.7 mg) of the recovered resin (205 mg) was treated with TFA/TIPS/H$_2$O (95:2.5:2.5) (0.2 mL) for 3 h to give the crude glycosylpeptide.

The crude material was purified by semi-preparative RP-HPLC and freeze-dried to afford a white fluffy solid (4.4 mg, 49%). $^1$H NMR (600 MHz, CD$_3$CN) δ 8.66 (d, J=2.4 Hz, 1H), 8.51 (dd, J=2.4, 8.4 Hz, 1H), 8.28 (d, J=7.8 Hz, 1H), 7.25 (d, J=7.8 Hz, 1H, Ser-NH), 7.17-7.15 (m, 3H, Ala-NH, Thr-NH, Val-NH), 6.82 (d, J=9.0 Hz, 1H, NHAc), 5.33 (d, J=1.8 Hz, 1H, H-4), 5.06 (dd, J=3.6, 11.4 Hz, 1H, H-3), 4.99 (d, J=3.0 Hz, 1H, H-1), 4.43 (dd, J=2.4, 8.4 Hz, 1H, Thr-α-CH), 4.39-4.36 (m, 1H, Ser-α-CH), 4.33-4.27 (m, 3H, Ala-α-CH, H-2, and H-5), 4.27-4.22 (m, 2H, Thr-β-CH and Ser-OH), 4.16 (dd, J=6.6, 7.8 Hz, Val-α-CH), 4.06 (s, 1H, H-6'), 4.05 (d, J=1.2 Hz, 1H, H-6), 3.97 (d, J=17.4 Hz, 1H, Gly-α-CH), 3.91 (d, J=17.4 Hz, 1H, Gly-α-CH), 3.74 (dd, J=5.4, 11.4 Hz, Ser-β-CH), 3.69 (dd, J=4.8, 11.4 Hz, Ser-β-CH), 2.09 (s, 3H, CH$_3$CO), 2.08-2.04 (m, 1H, Val-β-CH), 1.97 (s, 3H, CH$_3$CO), 1.90 (s, 3H, CH$_3$CO), 1.87 (s, 3H, CH$_3$CO), 1.36 (d, J=7.2 Hz, 3H, Ala-CH$_3$), 1.18 (d, J=6.6 Hz, 3H, Thr-CH$_3$), 0.90 (d, J=6.6 Hz, 3H, Val-CH$_3$), 0.88 (d, J=7.2 Hz, 3H, Val-CH$_3$); ESI-MS calcd for C$_{37}$H$_{52}$N$_8$NaO$_{22}$S 1015.28. found 1015.5.

Example 6

Solid Phase Synthesis of dNBS-Gly-Val-(Ac$_3$-Tn-α-Thr)-Ser-Ala-OH (5) (SEQ ID NO: 3) from Cleavage Using Reagent K A portion (18.4 mg) of the resin was treated with reagent K (TFA/thioanisole/H$_2$O/phenol/EDT=82.5:5:5:5:2.5) (0.2 mL) for 3 h. The resin was washed with neat TFA (2.4 mL), concentrated to dryness under reduced pressure, the residue washed with cold Et$_2$O four times and dried in high vacuum. Purification of the glycosylpeptide by semi-preparative RP-HPLC and after freeze-drying afforded a white fluffy solid (3.8 mg, 48%). The $^1$H NMR, ESI-MS and RP-HPLC trace were identical to the compound previously obtained with TFA/TIPS/H$_2$O treatment.

Example 7 dNBS-His-Gly-Val-(Ac$_3$-Tn-α-Thr)-Ser-Ala-OH (6)
(SEQ ID NO: 6)

After N-terminal capping with dNBS following the general procedure described earlier, a portion (70 mg) of the recovered resin (150 mg) was treated with TFA/TIPS/H$_2$O (95:2.5:2.5) (0.2 mL) for 3 h to give the crude glycosylpeptide. The crude material was purified by semipreparative RP-HPLC and freeze-dried to afford a white fluffy solid (20 mg, 56%). NMR (600 MHz, CD3CN) δ 8.98 (s, 1H, imidazole-NH), 8.62 (d, J=1.8 Hz, 1H, aromatic), 8.53 (dd, J=3.0, 8.4 Hz, 1H, aromatic), 8.41 (s, 1H, imidazole CH), 8.20 (d, J=8.4 Hz, 1H aromatic), 8.05 (t, J=6 Hz, 1H, Gly-NH), 7.88 (d, J=8.4 Hz, 1H, NH), 7.81 (d, J=6.6 Hz, 1H, NH), 7.77-7.71 (m, 1H, NH), 7.61-7.58 (m, 1H, NH), 7.23 (s, 1H, imidazole CH), 7.12 (d, J=12 Hz, 1H, AcNH), 7.01 (d, J=9.6 Hz, 1H, NH), 5.30 (d, J=3.0 Hz, 1H, H-4), 5.07 (dd, J=3, 11.4 Hz, 1H, H-3), 5.00 (d, J=3.6 Hz, 1H, H-1), 4.54-4.50 (m, 1H, Thr-α-CH), 4.43-4.37 (m, 1H, Ser-α-CH), 4.29-4.22 (m, 3H, Ala-α-CH, H-2 and H-5), 4.05 (d, J=6.00, 1H, His-α-CH), 3.90-3.85 (m, 2H, Thr-β-CH, Ser-OH), 3.78-3.76 (m, 1H, Val-α-CH), 3.71-3.70 (m, 2H, H-6), 3.26-3.23 (m, 2H, Ser-β-CH), 3.16-3.12 (m, 2H, His-β-CH), 2.10 (s, 3H, CH3CO), 1.97-1.94 (m, 7H, Val-β-CH, 2 CH3CO), 1.90 (s, 3H, CH3CO), 1.88 (d, J=5.4, 3H, Ala-CH3), 1.34 (d, J=7.2, 3H, Thr-CH3), 1.22 (dd, J=6.6, 15.6 Hz, 3H, Val-CH3), 0.89 (dd, J=6.6, 22.2, 3H, Val-CH3); mass spectrum (ESI-MS), m/z=1130.5 [M+H]+ (C43H60N11O23S requires 1130.35).

Example 8

N-α-N-Fmoc-N-im-Trityl-Protected L-Histidine
Trityl Thioester (7)

Fmoc protected N(trityl)-histidine (0.177 g, 0.29 mmol), HATU (0.166 g, 0.44 mmol) and tritylmercaptan (0.087 g, 0.31 mmol) were dried in vacuum for 30 minutes and to this dried mixture dry DMF (1.0 mL) was added followed by DIEA (0.20 mL, 1.26 mmol). The resulting solution was stirred for 2 h and completion of the reaction was confirmed by TLC. The reaction mixture was diluted with ethyl acetate (20 mL), washed with water (2×10 mL) and NaCl (1×10 mL). The organic layer was dried over sodium sulfate and concentrated under reduced pressure. The crude material was purified by flash column chromatography on SiO2 using stepwise gradient of acetone-ethyl acetate-hexane (5:5:90 and 10:10:80) to provide a colorless powder. Yield: 0.231 g (92%); TLC Rf=0.09 (acetone-ethyl acetate-hexane=7.5:7.5:85); 1H$^1$H NMR (600 MHz, CDCl3): δ 7.73 (d, J=7.8 Hz, 2H, aromatic H), 7.26 (t, J=9.0, 2H, aromatic H), 7.39 (s, 1H, imidazole H),7.35 (t, J=7.8 Hz, 2H, aromatic H), 7.31-7.25 (m, 8H, aromatic H), 7.22-7.08 (m, 24H, aromatic H), 7.02 (d, J=7.8 Hz, 1H, NH), 6.61 (s, 1H, imidazole H), 4.58 (q, J=7.8 Hz, 1H, α-CH), 4.45 (dd, J=6.0, 9.0 Hz, 1H, Fmoc CH), 4.55-4.40 (m, 2H, Fmoc CH2), 2.95 (d, J=5.4, 2H, β-CH); $^{13}$C NMR (150 MHz, CDCl3): δ 198.43 (SC═O), 156.23, 144.17, 144.03, 143.88, 142.48, 141.38, 141.36, 138.96, 136.19, 130.04, 129.96, 128.27, 128.25, 127.83, 127.77, 127.75, 127.24, 127.20, 127.10, 125.62, 125.46, 120.04, 119.59, 75.50, 70.11, 67.48, 61.25, 47.28, 29.88; mass spectrum (ESI-MS), m/z=878.0 [M+H]+ (C59H49N3O3S requires 878.3).

Example 9

Fmoc-His-SH (8)

The N-α-N-Fmoc-N-im-Trityl-Protected L-Histidine Trityl Thioester (0.2 g) was treated with cleavage cocktail of TFA-TIPS-$CH_2Cl_2$ (50:5:45) for 15 minutes under N2 atmosphere. The mixture was concentrated to dryness under reduced pressure and the crude material was kept under high vacuum for an hour. The desired thioacid was detected by ESI-MS and the crude was directly taken to the thioacid-dNBS ligation reaction without any further purification.

Example 10

Solid Phase Synthesis of Fmoc-Pro-Ala-OH (9)

The Fmoc-Pro-OH was manually assembled on a H2N-Ala preloaded 2-chlorotrityl resin (0.1 g) using Fmoc strategy. The reaction was performed in a 20 mL syringe reactor cartridge with agitation provided by a stream of N2. The synthesis involved the following steps: (i) coupling of Fmoc-Pro-OH (4 eq) for 3 h with pre-activation (2 min) in PyBOP (4 eq), HOBt (4 eq), DIEA (8 eq) and DMF (0.5 mL); (ii) Kaiser test; (iii) washing with DMF (3×3 mL, 5 min/wash). (iv) washing with DMF (3×3 mL, 5 min/wash followed by $CH_2Cl_2$ (3×3 mL, 5 min/wash) Double coupling was performed to achieve a complete reaction. The resin was treated with cleavage cocktail of TFE-AcOH-$CH_2Cl_2$ (2:2:6) (3 mL) for 4 h at room temperature under N2 atmosphere followed by washing the resin with a liberal amount of $CH_2Cl_2$. Evaporation of the solvents from the washings gave a thick oil which after a couple of co-evaporation with toluene afforded the desired dipeptide as a white solid. The purity of the product was satisfactory enough according to TLC, ESI-MS and 1HNMR and it was directly used for the next step without further purification. Yield: 0.026 g (91%). TLC Rf=0.3 (methanol-dichloromethane=1:9). This compound was reported in the literature. ‡‡Basak A.; Bag S. S.; Basak A.; *Bioorg. Med. Chem.*, 2005, 13, 4096-4102.

Example 11

Fmoc-Pro-Ala-SH (10)

To a solution of CDI (0.025 g, 0.159 mmol) in $CH_2Cl_2$ (1 mL) a solution of Fmoc-Pro-Ala-OH (0.013 g, 0.0318 mmol) in $CH_2Cl_2$ (1.5 mL) was added and stirred for 30 min under N2 atmosphere. Then NaHS was added to the mixture and the mixture was stirred for another 3 h under N2 atmosphere. The completion of the reaction was confirmed by ESI-MS monitoring. The reaction mixture was diluted with $CH_2Cl_2$ (6 mL) and the pH was brought to 3 by adding ice cold 1(N) HCl. The organic layer was immediately separated, washed with brine and dried over sodium sulfate. Evaporation of the solvent afforded the desired crude product as yellowish white semisolid (0.010 g, 74%). It was directly used in the thioacid-dNBS ligation reaction without further purification. Mass spectrum (ESI-MS), m/z=447.4 [M+Na]+ (C23H24N2O4SNa requires 447.5).

General Procedure for Thioacid-dNBS Ligation:

To a DMF solution of peptidyl thioacid (1.2 eq), Cs2CO3 (2 eq) was added followed by DMF solution of the dNBSpeptide (1 eq). The reaction mixture is stirred for 15 minutes under N2 atmosphere at room temperature. The completion of the reaction was monitored by ESI-MS. The DMF was co-evaporated with toluene under reduced pressure to get the crude peptide as yellowish semisolid. The crude material was purified by semi-preparative RP-HPLC and freeze-dried to afford the pure product.

Example 12

N-Fmoc-His-Gly-Val-(Ac$_3$-Tn-α-Thr)-Ser-Ala-OH (11) (SEQ ID NO: 4)

To a DMF (0.1 mL) solution of Fmoc-His-SH (0.84 mg, 0.0020 mmol) Cs2CO3 (1.1 mg, 0.0034 mmol) was added followed by DMF solution of the dNBS-Gly-Val-(Ac$_3$-Tn-α-Thr)-Ser-Ala-OH (SEQ ID NO: 3) (1.7 mg, 0.0017 mmol) The reaction mixture was stirred for 15 minutes under N2 atmosphere at room temperature. The completion of the reaction was monitored by ESI-MS. The DMF was co-evaporated with toluene under reduced pressure to get the crude peptide as yellowish semisolid. The crude material was purified by semi-preparative RP-HPLC and freeze-dried to afford the pure product. Yield: 1.4 mg (71%). $^1$H NMR (600 Mhz, CD3OD): δ 8.71 (s, 1H, imidazole H), 7.81 (d, J=7.2 Hz, 2H), 7.62 (d, J=7.8 Hz, 2H), 7.40 (t, J=7.2 Hz, 2H), 7.33-7.30 (m, 2H), 7.22 (s, 1H, imidazole H), 7.02 (d, J=9.0 Hz, 1H, NH), 6.65 (d, J=8.4 Hz, 1H, NH), 5.34 (s, 1H, H-4), 5.14 (dd, J=3.0, 11.4 Hz, 1H, H-3), 5.11 (d, J=4.2 Hz, 1H, H-1), 4.63 (s, 1H, Thr-α-CH), 4.50 (t, J=4.8 Hz, 1H, Ser-α-CH), 4.48-4.40 (m, 3H, His-α-CH & Fmoc CH2), 4.39-4.34 (m, 2H, H-2, Ala-α-CH), 4.30-4.28 (m, 3H, Thr-β-CH & 2 other protons), 4.20 (t, J=6.0 Hz, 1H, Fmoc CH), 4.09-4.03 (m, 2H), 3.97 (d, J=5.4, 2H, Gly-CH2), 3.82 (dd, J=4.8, 11.4 Hz, 1H, Ser-β-CH), 3.14-3.09 (m, 2H, His-β-CH), 2.19-2.17 (m, 1H, Val-β-CH), 2.14 (s, 3H, CH3CO), 2.00 (s, 3H, CH3CO), 1.97 (s, 3H, CH3CO), 1.93 (s, 3H, CH3CO), 1.42 (d, J=7.8 Hz, Ala-CH3), 1.28 (d, J=6.6 Hz, Thr-CH3), 1.00 (d, J=7.2 Hz, 3H, Val CH3), 0.99 (d, J=7.2 Hz, 2H, Val-CH3); Mass spectrum (ESI-MS), m/z=1122.3 [M+H]+ (C52H68N9O19 requires 1122.5).

Example 13

Fmoc-Pro-Ala-His-Gly-Val-(Ac$_3$-Tn-α-Thr)-Ser-Ala-OH (12) (SEQ ID NO: 5)

To a DMF (0.1 mL) solution of Fmoc-Pro-Ala-SH (1.53 mg, 0.0036 mmol) Cs2CO3 (1.95 mg, 0.006 mmol) was added followed by DMF solution of the dNBS-His-Gly-Val-(Ac$_3$-Tn-α-Thr)-Ser-Ala-OH (SEQ ID NO: 6) (3.5 mg, 0.003 mmol) The reaction mixture was stirred for 15 minutes under N2 atmosphere at room temperature. The completion of the reaction was monitored by ESI-MS. The DMF was co-evaporated with toluene under reduced pressure to get the crude peptide as yellowish semisolid. The crude material was purified by semi-preparative RP-HPLC and freeze-dried to afford the pure product. Yield: 2.05 mg (67%). Mass spectrum (ESI-MS), m/z=1291.1 [M+H]+ (C60H80N11O21 requires 1290.55).

The Scheme 1 (FIG. 26) explains the reaction mechanism of the sulfonamide-thioacid ligation to form amide bond.

The Scheme 2 (FIG. 27) shows the general strategy for the synthesis of Npeptidylsulfonamides on solid phase and the Scheme 3 (FIG. 28) demonstrates the general strategy for mixed phase synthesis of peptide sequences. The structures and yields for compounds 2-6 are shown in Table 1 (FIG. 29). Characterization data for compounds 1-7 and 9-12 are shown in FIGS. 1-25.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

Citation of any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

What is claimed is:

1. A peptide or peptide conjugate formed by a method of attaching amino acids to a growing peptide having an N-terminus using a solid-phase or a fluorous support, wherein the method comprises:
   attaching at least one sulfonamide group directly to the N-terminus of the growing peptide; and
   ligating the N-terminus with a peptidyl thio acid to produce a peptide or peptide conjugate, wherein the at least one sulfonamide group is removed during the ligation.

2. A method for synthesizing a peptide or peptide conjugate, comprising: attaching a 2,4-dinitrobenzenesulfonamide (dNBS) group or other sulfonamide group directly to an N-terminus of a growing peptide on a resin or a fluorous tag without the need to synthesize dNBS or other sulfonamide-modified amino acids or peptides; attaching a 2,4-dinitrobenzenesulfonamide (dNBS) group or other sulfonamide group site specifically to any position of an amino acid side chain during a solid-phase peptide synthesis; or a combination thereof.

3. The method of claim 2, comprising attaching a 2,4-dinitrobenzenesulfonamide (dNBS) group or other sulfonamide group directly to an N-terminus of a growing peptide on a resin or a fluorous tag without the need to synthesize dNBS or other sulfonamide-modified amino acids or peptides.

4. The method of claim 2, comprising attaching a 2,4-dinitrobenzenesulfonamide (dNBS) group or other sulfonamide group site specifically to any position of an amino acid side chain during a solid-phase peptide synthesis.

5. The method of claim 2, comprising attaching a 2,4-dinitrobenzenesulfonamide (dNBS) group or other sulfonamide group directly to an N-terminus of a growing peptide on a resin or a fluorous tag without the need to synthesize dNBS or other sulfonamide-modified amino acids or peptides, and attaching a 2,4-dinitrobenzenesulfonamide (dNBS) group or other sulfonamide group site specifically to any position of an amino acid side chain during a solid-phase peptide synthesis.

6. The method of claim 2, wherein the dNBS group or other sulfonamide group remains intact through a cleavage step of the peptide from the resin in order to affect a desired amide bond formation reaction with a thioacid off resin.

7. The method of claim 2, further comprising coupling the dNBS- or other sulfonamide-modified peptide with a thioacid while the dNBS- or other sulfonamide-modified peptide remains attached to a resin or a fluorous tag.

8. A 2,4-dinitrobenzenesulfonamide (dNBS)-modified peptide formed by: attaching a 2,4-dinitrobenzenesulfonamide (dNBS) group directly to an N-terminus of a growing peptide on a resin or a fluorous tag without synthesizing dNBS-modified amino acids or peptides; attaching a 2,4-dinitrobenzenesulfonamide (dNBS) group site-specifically to any position of an amino acid side chain during a solid-phase peptide synthesis; or a combination thereof.

9. A compound having the formula III:

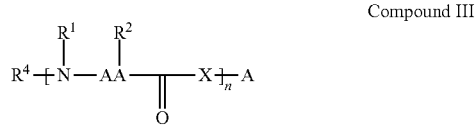

Compound III wherein

A is a solid-phase or fluorous support, or a linker grafted to a solid-phase or fluorous support or hydrogen;

X is O, OH, NH, $NH_2$, $NR^1$, or $NHR^1$, wherein $R^1$ is independently a hydrogen, $C_{1-n}$ alkyl, $C_{1-n}$ alkoxyl, or aryl-substituted $C_{1-n}$ alkyl;

AA is an optimally protected amino acid or optimally protected peptide, or

AA is an unprotected amino acid or unprotected peptide;

n is a positive integer;

$R^2$ represents any optimally protected or unprotected natural or unnatural amino acid side chain, the side chain containing a sulfonamide moiety selected from:

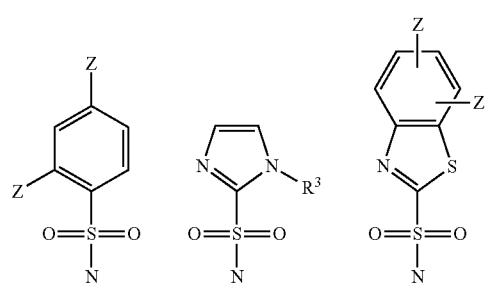

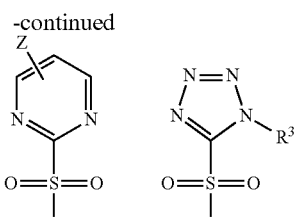

wherein, in $R^2$, Z is independently $NO_2$, $CF_3$, —COR, or F; R is $NH_2$, $C_{1-n}$ alkyl, or other electron withdrawing group; $R^3$ is $C_{1-n}$ alkyl, or aryl-substituted $C_{1-n}$ alkyl; and, N is part of a primary or secondary sulfonamide;

wherein, $R^4$ represents an amine protecting group orthogonal to the bond between X and A, hydrogen, or moiety:

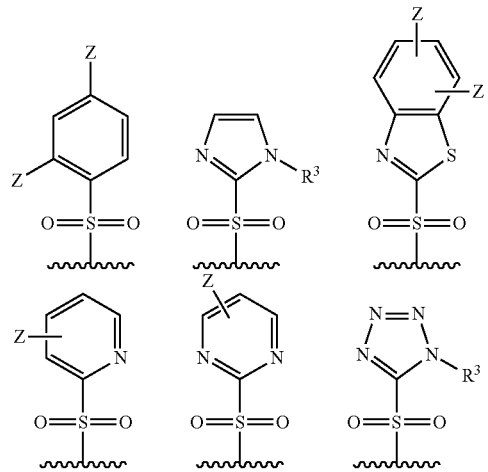

wherein, in $R^4$, Z is independently $NO_2$, $CF_3$, —COR, or F; R is $NH_2$, $C_{1-n}$ alkyl, or other electron withdrawing group; and $R^3$ is $C_{1-n}$ alkyl, or aryl-substituted $C_{1-n}$ alkyl; and wherein either:

(i) n is an integer between one and fifty, or (ii) AA is an unprotected amino acid.

10. The compound of claim 9, which has at least three amino acid units and contains at least one sulfonamide group.

11. The compound of claim 9, wherein n is an integer between one and fifty.

12. The compound of claim 9, wherein A is hydrogen.

13. The compound of claim 9, wherein AA is an unprotected amino acid.

14. The compound of claim 9, wherein AA is an unprotected peptide.

15. The compound of claim 9, wherein Z is $NO_2$.

16. A compound selected from the group consisting of:
dNBS-Alanine;
dNBS-Ser-Ala-OH;
dNBS-Val-Thr-Ser-Ala-OH (SEQ ID NO: 1);
dNBS-Gly-Val-Thr-Ser-Ala-OH (SEQ ID NO: 2);
dNBS-Gly-Val-($Ac_3$-Tn-α-Thr)-Ser-Ala-OH (SEQ ID NO: 3);
N-α-Fmoc-N-im-Trityl-Protected L-Histidine Trityl Thioester;
Fmoc-Pro-Ala-SH;
N-Fmoc-His-Gly-Val-($Ac_3$-Tn-α-Thr)-Ser-Ala-OH (SEQ ID NO: 4); and
Fmoc-Pro-Ala-His-Gly-Val-($Ac_3$-Tn-α-Thr)-Ser-Ala-OH (SEQ ID NO: 5).

17. The compound of claim 16, which is dNBS-Alanine.

18. The compound of claim 16, which is dNBS-Ser-Ala-OH.

19. The compound of claim 16, which is dNBS-Val-Thr-Ser-Ala-OH (SEQ ID NO: 1).

20. The compound of claim 16, which is dNBS-Gly-Val-Thr-Ser-Ala-OH (SEQ ID NO: 2).

21. The compound of claim 16, which is dNBS-Gly-Val-($Ac_3$-Tn-α-Thr)-Ser-Ala-OH (SEQ ID NO: 3).

22. A compound comprising dNBS-His-Gly-Val-($Ac_3$-Tn-α-Thr)-Ser-Ala-OH (SEQ ID NO: 6).

23. The compound of claim 16, which is N-α-Fmoc-N-im-Trityl-Protected L-Histidine Trityl Thioester.

24. The compound of claim 16, which is Fmoc-Pro-Ala-SH.

25. The compound of claim 16, which is N-Fmoc-His-Gly-Val-($Ac_3$-Tn-α-Thr)-Ser-Ala-OH (SEQ ID NO: 4).

26. The compound of claim 16, which is Fmoc-Pro-Ala-His-Gly-Val-($Ac_3$-Tn-α-Thr)-Ser-Ala-OH (SEQ ID NO: 5).

* * * * *

```
                        SEQUENCE LISTING

<160> NUMBER OF SEQ ID NOS: 6

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term dNBS
<220> FEATURE:
<223> OTHER INFORMATION: C-term -OH

<400> SEQUENCE: 1

Val Thr Ser Ala
1

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term dNBS
<220> FEATURE:
<223> OTHER INFORMATION: C-term -OH

<400> SEQUENCE: 2

Gly Val Thr Ser Ala
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term dNBS
<220> FEATURE:
<221> NAME/KEY: MOD_RES
<222> LOCATION: (3)..(3)
<223> OTHER INFORMATION: Ac3-Tn-alpha-Thr
<220> FEATURE:
<223> OTHER INFORMATION: C-term -OH

<400> SEQUENCE: 3

Gly Val Thr Ser Ala
1               5

<210> SEQ ID NO 4
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term N-Fmoc
<220> FEATURE:
<221> NAME/KEY: MOD_RES
<222> LOCATION: (4)..(4)
<223> OTHER INFORMATION: Ac3-Tn-alpha-Thr
<220> FEATURE:
<223> OTHER INFORMATION: C-term -OH

<400> SEQUENCE: 4

His Gly Val Thr Ser Ala
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (6)..(6)
<223> OTHER INFORMATION: Ac3-Tn-alpha-Thr
<220> FEATURE:
<223> OTHER INFORMATION: C-term -OH

<400> SEQUENCE: 5

Pro Ala His Gly Val Thr Ser Ala
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term dNBS
<220> FEATURE:
<221> NAME/KEY: MOD_RES
<222> LOCATION: (4)..(4)
<223> OTHER INFORMATION: Ac3-Tn-alpha-Thr
<220> FEATURE:
<223> OTHER INFORMATION: C-term -OH

<400> SEQUENCE: 6

His Gly Val Thr Ser Ala
1               5
```